(12) United States Patent
Dixon et al.

(10) Patent No.: US 7,167,851 B2
(45) Date of Patent: Jan. 23, 2007

(54) ONE DIMENSIONAL MOLECULAR REPRESENTATIONS

(75) Inventors: Steven L. Dixon, Yardley, PA (US); Kenneth M. Merz, Jr., Yardley, PA (US); Marvin Waldman, San Diego, CA (US)

(73) Assignee: Accelrys Software Inc., San Diego, CA (US)

(*) Notice: Subject to any disclaimer, the term of this patent is extended or adjusted under 35 U.S.C. 154(b) by 986 days.

(21) Appl. No.: 09/773,281

(22) Filed: Jan. 31, 2001

(65) Prior Publication Data

US 2003/0055802 A1    Mar. 20, 2003

(51) Int. Cl.
*G06F 17/00* (2006.01)
*G06N 5/02* (2006.01)
(52) U.S. Cl. .................. 706/48; 702/27; 703/12
(58) Field of Classification Search .......... 706/48; 702/27; 703/12
See application file for complete search history.

(56) References Cited

U.S. PATENT DOCUMENTS

| 6,295,514 B1 * | 9/2001 | Agrafiotis et al. ............ 703/12 |
| 6,421,612 B1 * | 7/2002 | Agrafiotis et al. ............ 702/19 |
| 6,453,246 B1 * | 9/2002 | Agrafiotis et al. ............ 702/27 |
| 6,571,227 B1 * | 5/2003 | Agrafiotis et al. ............ 706/15 |

OTHER PUBLICATIONS

Ramon Carbo, How Similar is aMolecule to Another? An Electron Density Measure of Similarity between Two Molecular Structures, 1980, Journal of Quantum Chemistry, vol. XVII, 1185-1189.*
*A General Method Applicable to the Search for Similarities in the Amino Acid Sequence of Two Proteins*, Saul B. Needleman and Christian D. Wunsch, J. Mol. Biol. (1970) 48. 443-453.
*Reduced Dimensional Representations of Molecular Structure*, Daniel D. Robinson, Thomas W. Barlow, and W. Graham Richards, J. Chem. Inf. Comput. Sci. 1997, 37, 939-942.
*The Utilization of Reduced Dimensional Representations of Molecular Structure for Rapid Molecular Similarity Calculations*, Daniel D. Robinson, Thomas W. Barlow, and W. Graham Richards, J. Chem. Inf. Comput. Sci. 1997, 37, 943-950.
*Alignment of 3D-Structures by the Method of 2D-Projections*, Daniel D. Robinson, Paul D. Lyne, and W. Graham Richards, J. Chem. Inf. Comput. Sci. 1999, 39, 594-600.
*Three-Dimensional Quantitative Structure—Activity Relationships from Tuned Molecular Quantum Similarity Measures: Prediction of the Corticosteroid-Binding Globulin Binding Affinity for a Steroid Family*, David Robert, Lluis Amat, and Ramon Carbó-Dorca, J. Chem. Inf. Comput. Sci. 1999, 39, 333-344.
*How Similar is a Molecule to Another? An Electron Density Measure of the Similarity between Two Compounds:* Ramon Carbó; Luis Leyda, and Mariano Arnau, International Journal of Quantum Chemistry, vol. XVII, 1185-1189 (1980).

* cited by examiner

Primary Examiner—Joseph P. Hirl
(74) Attorney, Agent, or Firm—Knobbe Martens Olson & Bear LLP

(57) ABSTRACT

Molecules are represented as one dimensional strings of atoms having a linear position and a width. One dimensional representations are compared to assess the likelihood of similarity in chemical behavior.

13 Claims, 21 Drawing Sheets

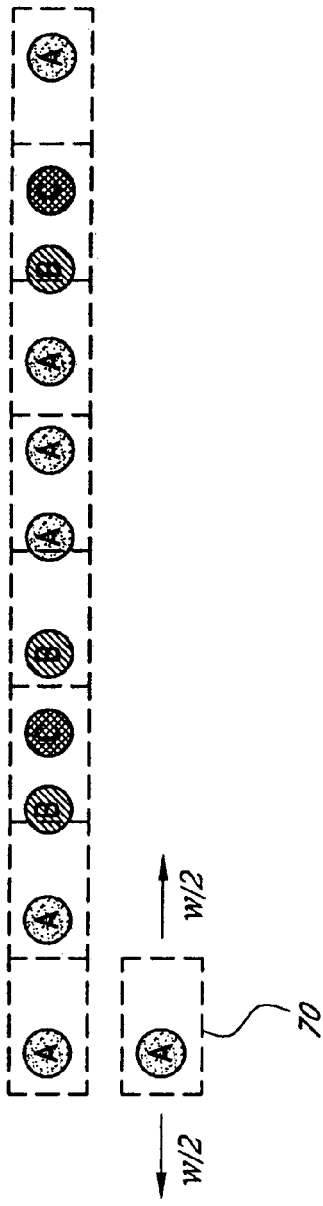
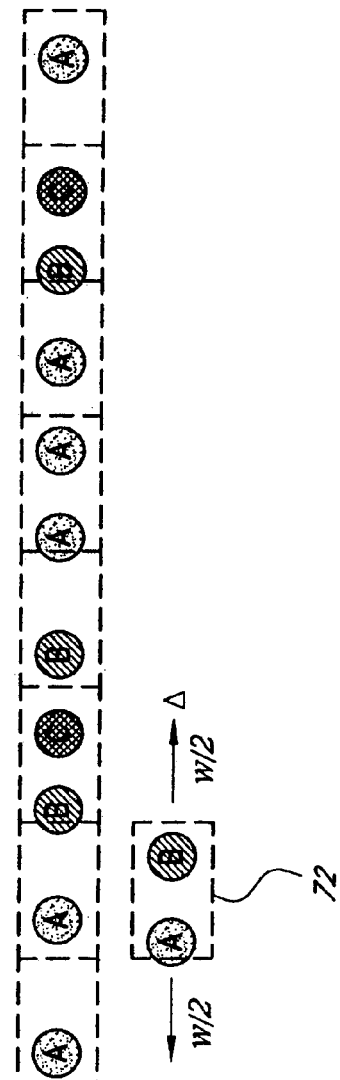
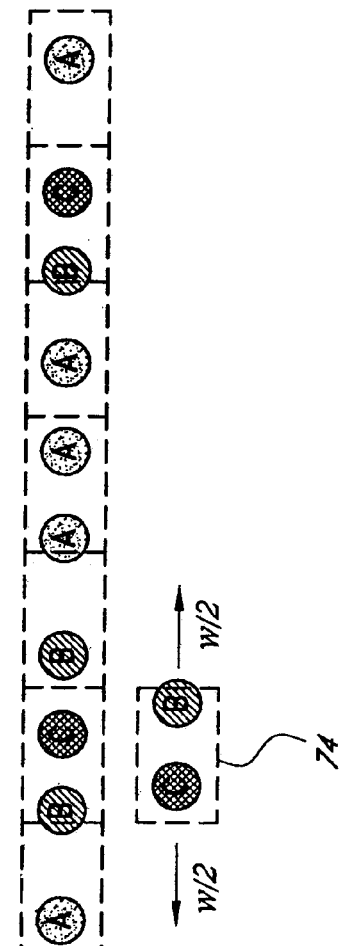
FIG. 7A
FIG. 7B
FIG. 7C

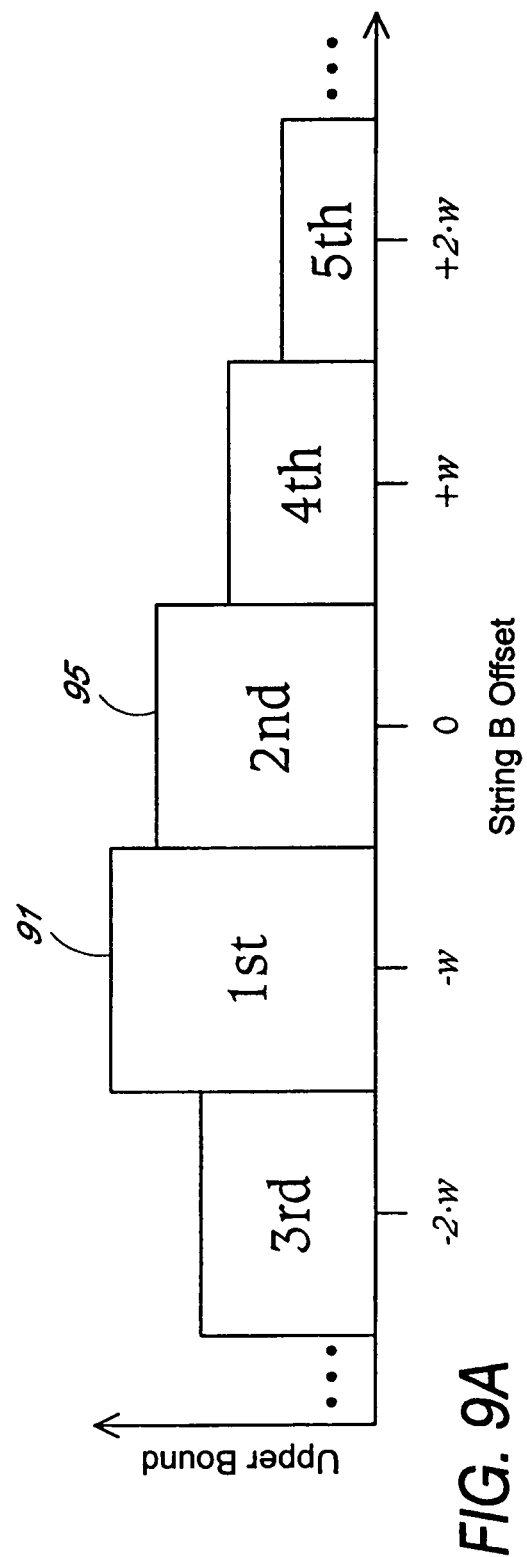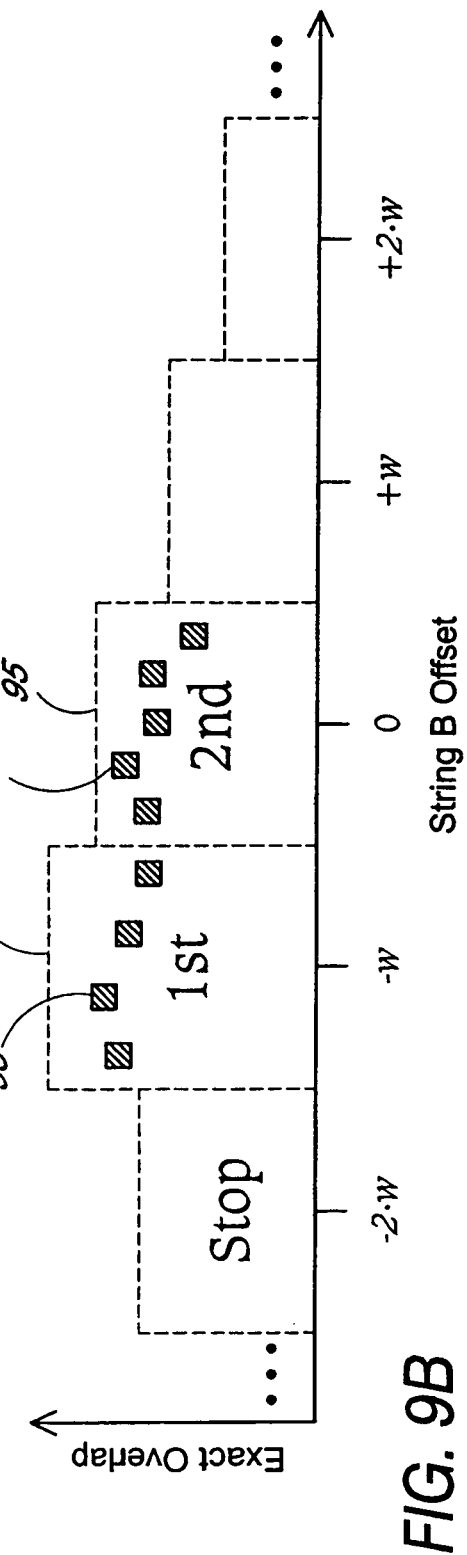
FIG. 9A
FIG. 9B

2D→1D

Compound A

Compound B1

3D→1D

2D→1D

Compound A

Compound B2

3D→1D

Speeding Up Bin-Based Overlap Calculations etc.

ONE DIMENSIONAL MOLECULAR REPRESENTATIONS

BACKGROUND OF THE INVENTION

1. Field of the Invention

The invention relates to methods and systems for performing molecular comparisons.

2. Description of the Related Art

Recent efforts to reduce the time and effort required to identify safe and effective pharmaceuticals have focused in part on attempts to characterize the behavior of drug candidate molecules without the need to actually perform chemical tests on the compounds. Generally, these efforts have focused on the prediction of molecular behavior by a computational analysis of chemical structure. Although this approach has not eliminated the need to perform chemical experiments, the amount of such testing can be considerably reduced by early identification of promising leads, and by eliminating from consideration compounds which are extremely unlikely to exhibit a particular desired chemical activity.

In many methods of computational analysis, physical molecular characteristics are reduced to a set of one or more descriptors. In some cases, the descriptor is related to a molecular characteristic that has been correlated to a certain chemical trait or behavior. One such example is molecular polar surface area, typically defined as the exposed van der Waals surface area of oxygen and nitrogen atoms (and attached hydrogens) in a molecule.

In some techniques, a set of molecules having unknown biochemical behavior is compared to a molecule having known biochemical behavior. Molecules that are in some sense more "similar" to the molecule with known activity are predicted to be more likely to exhibit similar chemical behavior.

One commonly used evaluation process of this type involves comparing the spatial arrangement of similar atoms in the two molecules. Although conceptually simple, this comparison process is difficult to implement due to the difficulty in ensuring an optimal relative orientation of the two molecules prior to any comparison of their atomic arrangements. Some attempts to simplify this comparison process have involved projecting a three dimensional molecule onto a two-dimensional plane, and performing a comparison of two-dimensional projections. This reduces the above mentioned orientation problem, but does not eliminate it entirely, as relative translation and rotation must still be optimized before a valid comparison can be made.

To date, analyzing large libraries of compounds using the above mentioned techniques remains time consuming and computationally expensive. Accordingly, the drug discovery process would be improved by new techniques to computationally evaluate potential chemical activity that operate faster, and that can screen chemical libraries with a smaller investment in time and/or processing power.

SUMMARY OF THE INVENTION

In one embodiment of the invention, a method of comparing molecules comprises representing each of two molecules as a set of selected atoms, wherein each atom of the set is associated with an atom type and a scalar value, wherein the set of scalar values is derived from distances between the selected atoms, and comparing the two molecules with respect to their atom types and scalar values. In some advantageous embodiments, the scalar value represents a linear position, and each atom of the set is associated with a second scalar value, the second scalar value representing a length centered about each of the linear positions. The comparison may comprise aligning the linear positions of an atom in the first molecule with an atom of the same type in the second molecule such that their lengths completely overlap and evaluating the amount of overlap between atoms of the first molecule and atoms of the same type of the second molecule.

In another embodiment, a method of molecular parameterization comprises selecting a set of atoms in the molecule, deriving a set of scalar values from distances between the selected atoms, and assigning to each of the selected atoms a parameter set including an atom type and one of the set of scalar values. A method of drug discovery may comprise comparing molecules that have been parameterized according to this method.

BRIEF DESCRIPTION OF THE DRAWINGS

FIGS. 7A–7C illustrate the measurement of individual segment overlaps within a range of independent motion of selected individual segments.

FIG. 9 illustrates the use of upper bound calculations to reduce the total number of overlap calculations required to determine the maximum overlap.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
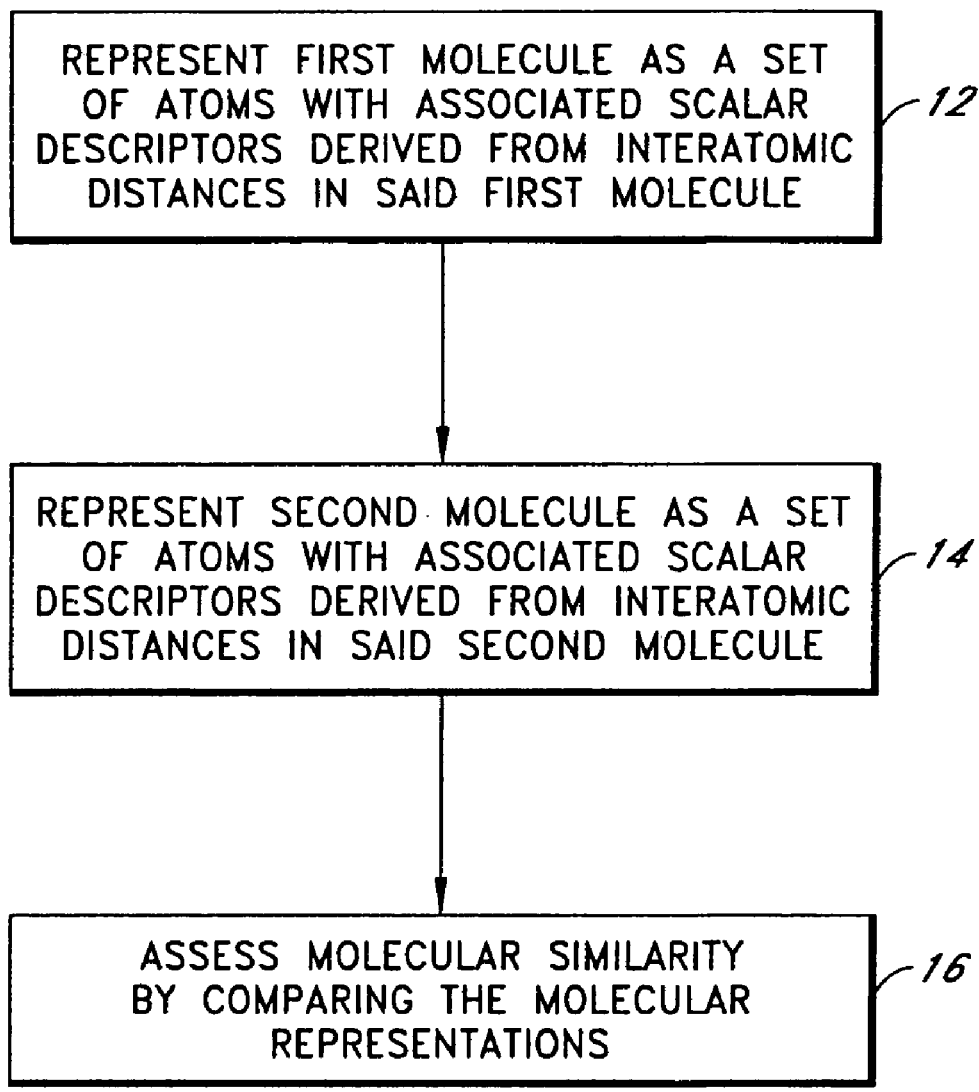
FIG. 1 is a flow chart of a method of assessing molecular similarity according to one embodiment of the invention.

Referring now to FIG. 1, a method for measuring molecular similarity begins at block 12, where a first molecule is represented as a set of atoms with associated scalar descriptors. The scalar descriptors may be derived from inter-atomic distances between the atoms of the molecule. Conceptually, each scalar descriptor can be thought of as an atomic position along a string, and this representation process may be described as forming a one-dimensional representation of the three-dimensional molecule. Of course, it is typically not possible, except perhaps with extremely simple molecules, to produce a one-dimensional representation where the inter-atomic distances in the one-dimensional representation are all equal to their corresponding three-dimensional distances in the actual molecule. But in one embodiment, the inter-atomic distances in the one-dimensional representation are selected such that the deviation between the one dimensional distances and the corresponding three dimensional distances is reduced with a procedure that is designed to produce a somewhat close "match" between the one-dimensional distances and the corresponding three dimensional distances.

In one such embodiment, therefore, an error metric $S^2$, defined as follows:

$$S^2 = \frac{\sum_{i>j}^{n} (|x_i - x_j| - d_{ij})^2}{\sum_{i>j}^{n} (d_{ij})^2}$$

is minimized with respect to $x_i$. The denominator is a constant with respect to any given molecule, but is useful for optimization purposes because it renders $S^2$ dimensionless, thus eliminating its dependence on the units with which distance is measured.

It may in some cases be advantageous to use alternative versions of $S^2$. For example, there are alternatives for this formula from the distance geometry literature which are also suitable for use in conjunction with the invention. Several of these can be found in "The Theory and Practice of Distance Geometry", T. F. Havel, I. D. Kuntz, and G. M. Crippen, Bull. Math. Biol., vol. 45, pp. 665–720 (1983), the entire disclosure of which is hereby incorporated by reference in its entirety. One such alternative function is:

$$S^2 = \sum_{i>j}^{n} \left[1 - \left(\frac{x_i - x_j}{d_{ij}}\right)^2\right]^2$$

Havel et al point out that this function exhibits good behavior for optimization purposes. Another possible function is:

$$S^2 = \sum_{i>j}^{n} \{1 - [\max(x_{ij}/d_{ij}, d_{ij}/x_{ij})]^2\}^2.$$

where $x_{ij} = x_1 - x_j$.

This function is convex in one dimension, and should thus optimize quite readily to the global minimum and avoid issues/complications involving local minima.

It may be noted that the formulas for $S^2$ above utilize distance values $d_{ij}$ between atom pairs of the molecule. If the atomic configuration is defined by three dimensional atomic coordinates relative to some defined origin, the distances $d_{ij}$ can be calculated arithmetically. In some cases, however, 3-D structural data such as may be obtained experimentally by x-ray crystallography or theoretically by quantum mechanical calculations is unavailable. In these cases, it is still typically possible to derive or estimate three-dimensional distances for use in formula 1 by using topological distances defined by inter-atomic bond types, lengths and/or angles. In some embodiments, a distance between two atoms could be numerically represented by simply counting the minimum number of bonds that must be traversed to travel from one atom to the other. This topological data may be referred to as 2-D molecular information, as the molecular topology necessary for deriving distances for use in the above formulas is available from a standard two-dimensional bonding diagram. In these cases, one can proceed solely from a knowledge of atomic connectivity of the molecule (molecular topology) to determine a set of distances to use in one of the formulas for $S^2$ presented above. The distance values used in the $S^2$ formula may thus be taken from either the: 1) actual distances between pairs of atoms from a 3D structural conformation, 2) estimated 3D distances between pairs of atoms using rules based on chemical topology, or 3) purely topological distances between a pair of atoms based on the minimum number of bonds needed to connect a path between the two atoms.

These different sources of $d_{ij}$ values may be suitable in different situations. One example mentioned above is when 3D distance data is unavailable for a molecule. Another consideration is the fact that a set of 3D distances will be representative of a single molecular conformation, when the molecule may exist in several different conformations. If molecular similarity is thought to be conformation dependent, starting with a 3D representation is likely more suitable. On the other hand, if it is desired that the molecular representations used in a similarity calculation be conformation independent, distances based on topology/connectivity may be more appropriate.

Given numerical values for the inter-atomic distances $d_{ij}$, a variety of mathematical optimization algorithms are well known and suitable for deriving the set of positions $x_i$ to form a suitable one-dimensional molecular representation. In most techniques, an initial estimate for each of the scalar descriptors $x_i$ is made, and these estimates are refined to minimize $S^2$. Although it is possible to initially select random values for the one-dimensional positions $x_i$, the minimization can be performed much faster if the initial estimates are at least somewhat close to the actual minimized values.

Whether the distances $d_{ij}$ are derived from 3D atomic coordinates or 2D topological information, the process of finding an initial estimate of the one dimensional atomic positions typically involves defining an axis through the molecule being represented, and choosing as the set of starting locations the distance along the axis between each atom and that molecular centroid. The best axis to use for this procedure is the axis that produces the largest total sum of the squared centroid to atom distances along the axis. This axis can be pictured as the one that lies along the longest dimension of the molecule, thus stretching out the initial one dimensional atomic locations as much as possible.

Mathematical techniques for defining this axis and deducing the set of starting positions have been devised. If 3D atomic positions are known, one such technique begins with finding the centroid of the arrangement of atomic positions. If the centroid is located at $(x_0, y_0, z_0)$, $v$ is defined as the initially unknown unit vector which will ultimately be the 1D axis we seek, and $p_{0i}$ is a vector which extends from the centroid to atom i, then the projection of $p_{0i}$ onto $v$ will be the initial 1D coordinate estimate for atom i and this is given by the scalar-valued dot product $p_{0i} \cdot v$:

$$p_{0i} \equiv \begin{bmatrix} x_i - x_0 \\ y_i - y_0 \\ z_i - z_0 \end{bmatrix}, \quad v \equiv \begin{bmatrix} v_1 \\ v_2 \\ v_3 \end{bmatrix}$$

$$x_i^{1D}(\text{estimate}) = p_{0i} \cdot v = (x_i - x_0)v_1 + (y_i - y_0)v_2 + (z_i - z_0)v_3$$

The elements of $v$ are chosen to maximize the sum of the squares of the projections (1D estimates) for all atoms i:

Maximize $$f(v_1, v_2, v_3) \equiv \sum_{i=1}^{n} (p_{0i} \cdot v)^2$$

with respect to $v_1, v_2, v_3$ subject to the constraint that $v$ have unit length:

$$1 = v \cdot v = \sum_{j=1}^{3} v_j^2$$

Thus $(v_1, v_2, v_3)$ will be some point that lies on the surface of the unit sphere. The standard means of doing this type of constrained optimization is to define a new function $L$ which links the constraint relation to the objective function $f$ by means of a scalar Lagrange multiplier $\lambda$:

$$L(v_1, v_2, v_3, \lambda) \equiv f(v_1, v_2, v_3) - \lambda \left( \sum_{j=1}^{3} v_j^2 - 1 \right)$$

The term multiplying $\lambda$ is zero provided the constraint is satisfied, thus $L$ may be thought of as the function $f$ restricted to just the points $(v_1, v_2, v_3)$ that lie on the surface of the unit sphere. The value of $\lambda$ is left undetermined until after we establish the family of solutions $v$. $L$ is maximized by setting to zero the partial derivatives with respect to $v_1$, $v_2$, and $v_3$, treating $\lambda$ as a constant:

$$0 = \frac{\partial L}{\partial v_1} = 2 \sum_{i=1}^{n} (x_i - x_0)[(x_i - x_0)v_1 + (y_i - y_0)v_2(z_i - z_0)v_3] - 2\lambda v_1$$

$$0 = \frac{\partial L}{\partial v_2} = 2 \sum_{i=1}^{n} (y_i - y_0)[(x_i - x_0)v_1 + (y_i - y_0)v_2(z_i - z_0)v_3] - 2\lambda v_2$$

$$0 = \frac{\partial L}{\partial v_3} = 2 \sum_{i=1}^{n} (z_i - z_0)[(x_i - x_0)v_1 + (y_i - y_0)v_2(z_i - z_0)v_3] - 2\lambda v_3$$

This is a 3×3 system of equations which may be compactly written in matrix-vector notation:

$$Gv = \lambda v$$

where $G = \sum_{i=1}^{n} \begin{bmatrix} (x_i - x_0)(x_i - x_0) & (x_i - x_0)(y_i - y_0) & (x_i - x_0)(z_i - z_0) \\ (y_i - y_0)(x_i - x_0) & (y_i - y_0)(y_i - y_0) & (y_i - y_0)(z_i - z_0) \\ (z_i - z_0)(x_i - x_0) & (z_i - z_0)(y_i - y_0) & (z_i - z_0)(z_i - z_0) \end{bmatrix}$ The solutions $v$ are the eigenvectors of $G$ and the scalar quantities $\lambda$ are the associated eigenvalues. These can be obtained using well-established numerical procedures. There will be three solutions: $(v^{<1>}, \lambda^{<1>})$, $(v^{<2>}, \lambda^{<2>})$, $(v^{<3>}, \lambda^{<3>})$, where the eigenvectors are mutually orthogonal and $\lambda^{<1>} \geq \lambda^{<2>} \geq \lambda^{<3>} \geq 0$. Note that any scalar multiple of an eigenvector is still an eigenvector, so we can simply scale the entries of $v$ to satisfy the constraint $v \cdot v = 1$. We choose $v^{<1>}$ as the initial 1D axis because it has the largest eigenvalue and thus yields the largest sum of squared projections:

$$\sum_{i=1}^{n} (p_{0i} \cdot v^{<1>})^2 = \sum_{i=1}^{n} [(x_i - x_0)v_1^{<1>} + (y_i - y_0)v_2^{<1>} + (z_i - z_0)v_3^{<1>}]^2$$

$$= v^{<1>} \cdot (Gv^{<1>}) = \lambda^{<1>} v^{<1>} \cdot v^{<1>}$$

$$= \lambda^{<1>} \text{ (due to the normalization constraint)}$$

This specific procedure would not be used when 3D atomic coordinates are not explicitly known. However, other techniques of defining an appropriate axis and generating starting values for one dimensional atomic positions may be utilized which use as a starting point only the set of distance values $d_{ij}$. In these embodiments, we do not know explicit coordinates for the centroid, but distance geometry tells us how to calculate the distance from each point to the centroid:

$$d_{0i}^2 = \frac{1}{n} \sum_{\mu=1}^{n} d_{i\mu}^2 - \frac{1}{n^2} \sum_{v > \mu=1}^{n} \sum d_{\mu v}^2$$

The distances $d_{0i}$ correspond to the lengths of the vectors $p_{0i}$ which we saw in the previous 3D→1D derivation.

The law of cosines can be applied to the angle formed by each pair of vectors $p_{0i}$ and $p_{0j}$:

$$\cos(\theta_{ij}) = \frac{d_{0i}^2 + d_{0j}^2 - d_{ij}^2}{2 d_{0i} d_{0j}}$$

Armed with this information, we are ready to define the unit vector v, which is the 1D axis we seek:

$$V = \sum_{j=1}^{n} v_j p_{0j}$$

Thus we are expressing v as some linear combination of the vectors $p_{01}, \ldots, p_{0n}$.

As in the case when 3D coordinates are initially known, the initial estimate for the 1D coordinate of atom i is given by the projection or dot product $p_{0i} \cdot v$:

$$x_i^{1D} \text{ (estimate)} = p_{0i} \cdot v = \sum_{j=1}^{n} v_j (p_{0i} \cdot p_{0j})$$

$$= \sum_{j=1}^{n} v_j \left( \frac{d_{0i}^2 + d_{0j}^2 - d_{ij}^2}{2} \right)$$

$$= \sum_{j=1}^{n} v_j [d_{0i} + d_{0j} \cos(\theta_{ij})]$$

We again want to maximize the sum of the squared projections:

Maximize $$f(v_1, \ldots, v_n) \equiv \sum_{i=1}^{n} (p_{0i} \cdot v)^2$$

with respect to $v_1, \ldots, v_n$

While constraining v to have unit length:

$$1 = v \cdot v = \left( \sum_{i=1}^{n} v_i p_{0i} \right) \cdot \left( \sum_{j=1}^{n} v_j p_{0j} \right) =$$

$$\sum_{i=1}^{n} \sum_{j=1}^{n} v_i v_j (p_{0i} \cdot p_{0j}) = \sum_{i=1}^{n} \sum_{j=1}^{n} v_i v_j \left( \frac{d_{0i}^2 + d_{0j}^2 - d_{ij}^2}{2} \right)$$

This constraint differs in appearance from the 3D→1D case because the entries of v are associated with the non-orthogonal vectors $p_{01}, \ldots, p_{0n}$ instead of the orthogonal Cartesian xyz axes. The constrained optimization is carried out on L:

$$L = \sum_{i=1}^{n} \left[ \sum_{j=1}^{n} v_j \left( \frac{d_{0i}^2 + d_{0j}^2 - d_{ij}^2}{2} \right) \right]^2 -$$

$$\lambda \left[ \sum_{i=1}^{n} \sum_{j=1}^{n} v_i v_j \left( \frac{d_{0i}^2 + d_{0j}^2 - d_{ij}^2}{2} \right) - 1 \right]$$

$$= \sum_{i=1}^{n} \left[ \sum_{j=1}^{n} v_i G_{ij} \right]^2 - \lambda \left[ \sum_{i=1}^{n} \sum_{j=1}^{n} v_i v_j G_{ij} - 1 \right] \text{ where}$$

$$G_{ij} \equiv \left( \frac{d_{0i}^2 + d_{0j}^2 - d_{ij}^2}{2} \right) = p_{0i} \cdot p_{0j}$$

For k=1, . . . , n, we require:

$$0 = \frac{\partial L}{\partial v_k} = 2 \sum_{i=1}^{n} \sum_{j=1}^{n} G_{ik} G_{ij} v_j - 2\lambda \sum_{i=1}^{n} G_{ik} v_i$$

This n×n system of equations can be rewritten in matrix-vector form:

$$G^T G v = \lambda G^T v \text{ Where } G_{ij}^T \equiv G_{ji}$$

or, $GGv = \lambda Gv$ because $G_{ji} = G_{ij}$

If we make the substitution y=Gv, then we have the following standard eigen-problem to solve:

$$Gy = \lambda y$$

We choose the eigenvector $y^{<1>}$ with the largest associated eigenvalue $\lambda^{<1>}$, and we back-solve to get the 1D axis $v^{<1>}$:

$$Gv^{<1>} = y^{<1>}$$

If we let $v^{<1>} = y^{<1>}/\lambda^{<1>}$, then we have a solution, because $$G\left( \frac{y^{<1>}}{\lambda^{<1>}} \right) = \frac{\lambda^{<1>} y^{<1>}}{\lambda^{<1>}} = y^{<1>}$$

The entries of $y^{<1>}$ have to be scaled so that the constraint on $v^{<1>}$ is satisfied:

$$1 = \sum_{i=1}^{n} \sum_{j=1}^{n} v_i^{<1>} v_j^{<1>} G_{ij}$$

$$= \sum_{i=1}^{n} \sum_{j=1}^{n} \left( \frac{y_i^{<1>}}{\lambda^{<1>}} \right) \left( \frac{y_j^{<1>}}{\lambda^{<1>}} \right) G_{ij}$$

$$= \sum_{i=1}^{n} \left( \frac{y_i^{<1>}}{\lambda^{<1>}} \right) \left( \frac{\lambda^{<1>} y_j^{<1>}}{\lambda^{<1>}} \right) \text{ because } Gy^{<1>} = \lambda^{<1>} y^{<1>}$$

$$= \frac{1}{\lambda^{<1>}} \sum_{i=1}^{n} (y_i^{<1>})^2$$

Hence, we require $$\sum_{i=1}^{n} (y_i^{<1>})^2 = \lambda^{<1>}$$

Once we have $y^{<1>}$ and hence $v^{<1>}$, we can compute the initial 1D estimates:

$$x_i^{1D} \text{ (estimate)} = p_{0i} \cdot v^{<1>} = \sum_{j=1}^{n} v_j^{<1>}(p_{0i} \cdot p_{0j})$$

$$= \sum_{j=1}^{n} \left(\frac{y_j^{<1>}}{\lambda^{<1>}}\right) G_{ij}$$

$$= \frac{\lambda^{<1>} y_i^{<1>}}{\lambda^{<1>}} = y_i^{<1>}$$

Therefore, the entries of $y^{<1>}$ are the initial 1D estimates.

It may be further noted that when 3D coordinates are explicitly known, they may be used to compute a set of distances $d_{ij}$ that can be used in the second method described above. In this case, the same result will be obtained as would result from an application of the first method using the explicit 3D coordinates.

Once the initial estimates of x for each atom has been calculated, a BFGS optimization procedure (see, e.g. Practical Methods of Optimization, Volume 1, Unconstrained Optimization; Wiley, New York, 1980) may then be performed to adjust the initial estimates so as to minimize $S^2$.

This process is of course easier to perform when there are fewer atoms to be considered, and it will be appreciated that in many cases not all of the atoms of a molecule need to be considered when creating the one-dimensional representation. Typically, hydrogens would be ignored, for example. If a particular molecular region or atom subset of the entire molecule is known to be primarily responsible for activity, such a molecule may be represented by a string representing the positions of only those atoms. It is also possible to weight the error between selected inter-atomic distances and their one-dimensional counterparts more than others during the optimization procedure. In one embodiment of this technique, smaller three-dimensional inter-atomic distances are matched more closely than remote inter-atomic distances in the one dimensional representation.

At block 14 of FIG. 1, the same scalar value representation procedure is performed on a second molecule which is to be compared to the first molecule. Finally, at block 16, molecular similarity between the two molecules is assessed by comparing the representations. Generally, this similarity assessment involves comparing the scalar values $x_i$ which are associated with atoms having the same type or classification. If two molecules have a relatively large number of similar atoms with similar associated scalar values $x_i$, the molecules receive a high similarity score.

The atoms can be classified in a variety of ways. In some suitable embodiments of the invention, atom classification is based on element type and hybridization state, but any other atomic characteristic, parameter, or descriptor such as electronegativity, charge state, polarization, polarizability, etc. could be used. It will also be appreciated that the "molecule" being represented in one dimension need not be a known chemical compound, but could be a pharmacophore having positions associated with atomic parameters or characteristics rather than with specific physical atoms.

As will be described in additional detail below with reference to FIGS. 3A–3C and 4, the comparison process can be performed surprisingly quickly, with a near total elimination of the molecular orientation problem mentioned above.

Figure 2:
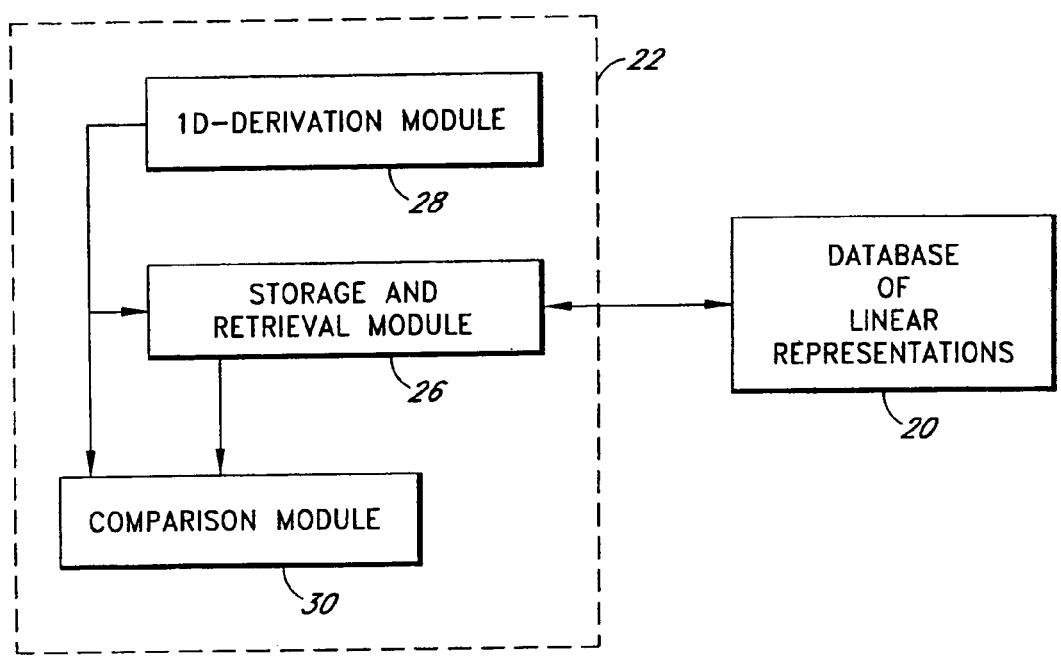
FIG. 2 is a block diagram of a system for assessing molecular similarity in accordance with one embodiment of the invention.

Turning now to FIG. 2, each atom in the representation may be stored in a database 20 as a character string encoding its atomic classification and its scalar descriptor $x_i$. The database 20 is coupled to a data processing system 22 such as a personal computer or workstation. The database 20 may of course be stored physically in the data processing system 22 on a computer readable medium such as a hard disk drive, or elsewhere on a local or wide area network, or on a piece of removable media such as a CD.

The data processing system will advantageously comprise several software modules. A storage and retrieval module 26 for storing and retrieving information from the database 20 is provided. A representation derivation module 28 is also advantageously provided for deriving the one-dimensional representations as described above. Also provided is a comparison module 30 for comparing the one-dimensional representations and computing similarity measures for molecule pairs.

Figure 3A:
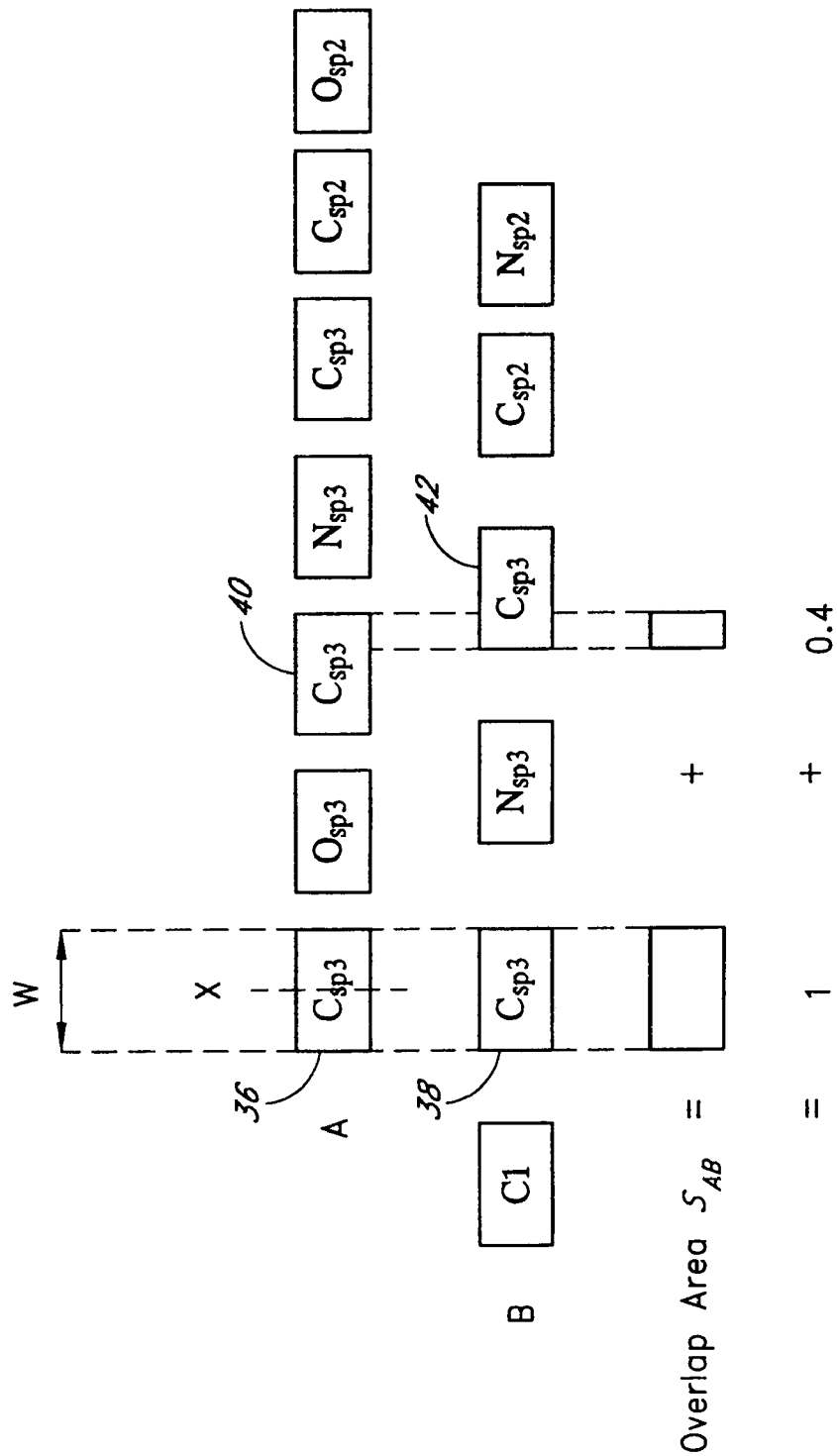
FIG. 3A is an illustration of a first one-dimensional alignment of molecular representations.
Figure 3B:
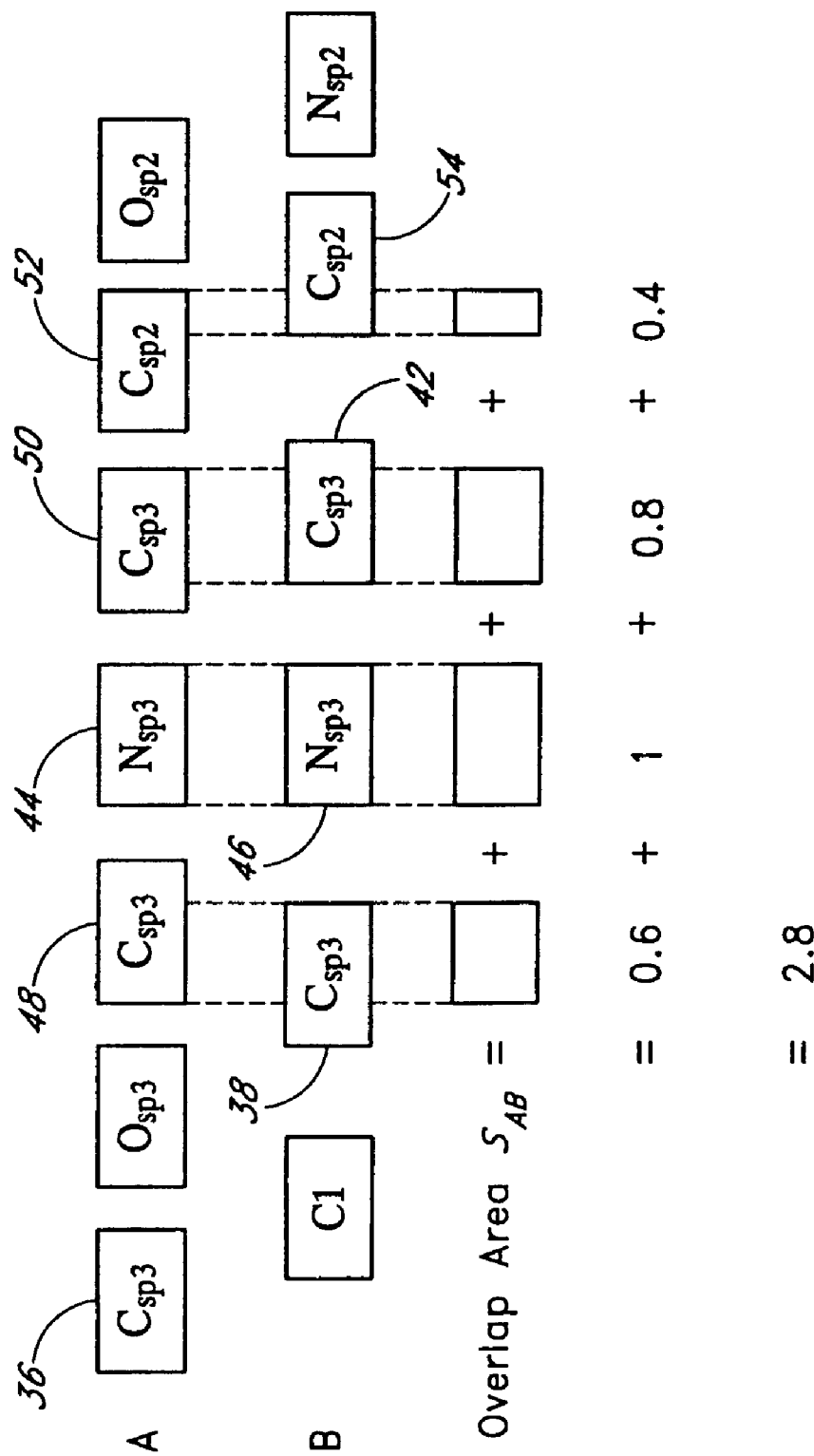
FIG. 3B is an illustration of a second one-dimensional alignment of molecular representations.
Figure 3C:
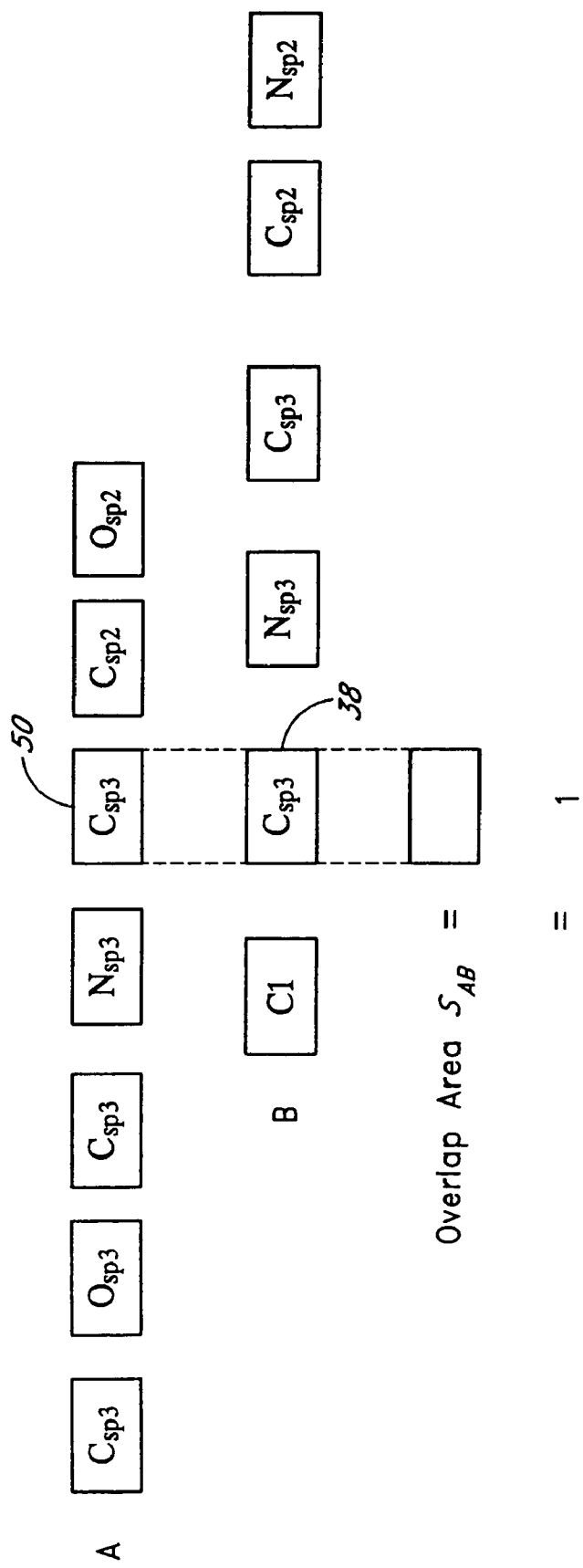
FIG. 3C is an illustration of a third one-dimensional alignment of molecular representations.

FIGS. 3A through 3C illustrate one advantageous comparison procedure for computing a similarity score between two one-dimensional molecular representations. In this embodiment, each atom is considered to extend from either side of its position by a selected amount, thereby defining not only an atomic position $x_i$, but also an atomic width, $w_i$. In one suitable embodiment, $w_i$ is the same for all atoms, and is set to one angstrom, although other atomic width values may be used. For clarity, in FIGS. 3A through 3C, the atomic widths do not overlap, but it will be appreciated that if the center positions $x_i$ of two atoms are within $w_i$, their widths will overlap within the string.

A suitable process for comparing two one-dimensional molecular representations may be conceptualized as laying the strings next to each other, sliding one string past the other in increments, and measuring the amount of atomic width overlap that occurs for atoms of the same type or class at each increment. As will be explained in more detail below, this process can be performed quickly because it can be shown that only a limited number of specific relative positions need to be considered to find the maximum overlap value.

This incremental sliding process is illustrated in FIGS. 3A through 3C, wherein string A and string B are example one dimensional representations of hypothetical molecules or portions of molecules. In FIG. 3A, string A and string B are aligned such that their leftmost sp3 hybridized carbons 36, 38 are exactly aligned, producing a one angstrom overlap for these two atoms. With this alignment, the only other overlap of atoms in the same class is the partial overlap of two more sp3 hybridized carbon atoms 40, 42 of about 0.4 angstroms.

FIG. 3B shows string B moved rightward until the sp3 hybridized nitrogen atoms 44, 46 are exactly aligned. In this configuration, there is overlap not only between the nitrogens 44, 46, but also between a first pair of sp3 hybridized carbon atoms 48, 38, a second pair of sp3 hybridized carbons 42, 50, and a pair of sp2 hybridized carbons 52, 54, thus producing approximately twice the total overlap of the configuration of FIG. 3A.

In FIG. 3C, string B is again moved rightward until there is exact overlap between rightmost sp3 carbon 50 of string A and the leftmost sp3 carbon 38 of string B. In this orientation, no additional overlaps of atoms of the same class are present, and the total overlap is again less than the overlap of the alignment of FIG. 3B.

It can be appreciated that if this process is performed beginning with string B fully to the left of string A and ending with string B fully to the right of string A, the total atomic width overlap will start at 0, end at 0, and have a maximum value somewhere in between the leftmost and rightmost positions. It is one advantageous aspect of this invention embodiment, however, that the overlap need not be evaluated continuously from one end to the other to find the maximum overlap. This is because the maximum overlap must occur at some point coinciding with the exact alignment of at least one atom pair of the same class. This fact can be appreciated by realizing that if the overlap is plotted as a function of position as one string is moved continuously along another, the maximum overlap will occur at a peak of the overlap curve, at which point a negative slope change occurs. Such a decrease in the slope of the overlap curve can only occur at the moment two atoms of the same class pass through perfect alignment such that their overlap begins to decrease. While negative slope changes can occur at positions other than the global maximum, it remains true that the global maximum will always occur at such a point. Thus, the overlap need only be evaluated at those discrete orientations where at least one atom pair of the same class is perfectly aligned.

Figure 4:
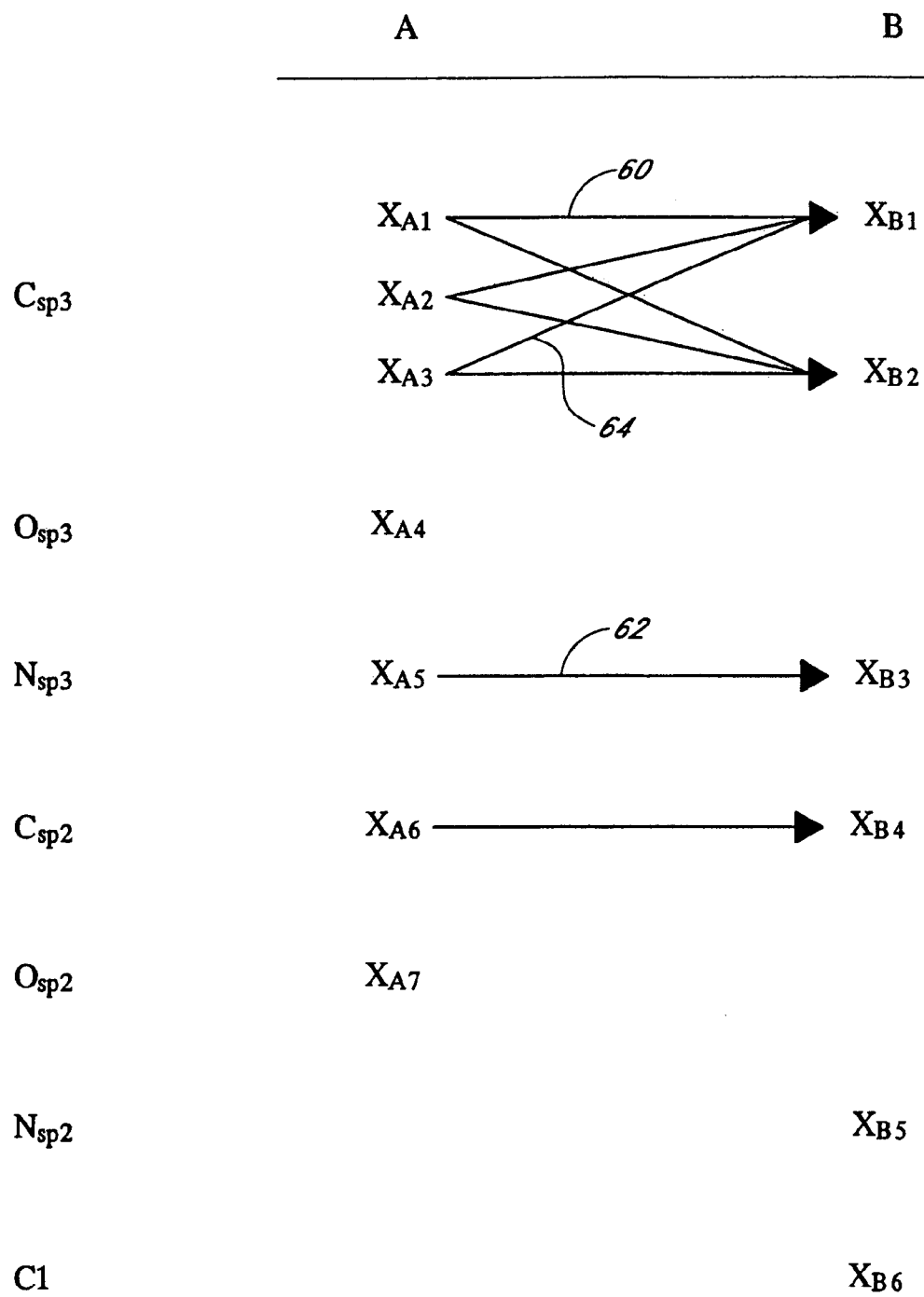
FIG. 4 illustrates the set of atomic alignments that potentially produce a maximum molecular similarity measure between the two molecules of FIGS. 3A–3C.

This principle is illustrated in FIG. 4 using the strings of FIGS. 3A through 3C. In FIG. 4, the first column contains the list of atomic classifications, the second column contains the atomic positions $X_{A1}$ through $X_{A7}$ for each atom class in string A, and the third column contains the atomic positions $X_{B1}$ through $X_{B6}$ for each atom class in string B. In this example, string A has three sp3 hybridized carbons (located at positions $X_{A1}$, $X_{A2}$, and $X_{A3}$), and string B has two (located at positions $X_{B1}$ and $X_{B2}$). Separately aligning each of the three sp3 carbons of string A with the two sp3 carbons of string B defines six string alignments to be considered. In addition, each of the strings has an sp3 nitrogen and an sp2 carbon, resulting in two more alignments to be considered for a total of eight. The orientations of FIGS. 3A, 3B, and 3C are represented by arrows 60, 62, and 64 respectively in FIG. 4. Thus, by evaluating the overlap at these eight discrete relative string positions, the maximum overlap for all possible orientations of these two strings is guaranteed to be found.

It may be noted that if a molecule is represented by a linear string of atomic positions as described above, the mirror image of that string is an equivalent representation of the molecule. However, the mirror image of a string may show a different maximum overlap with another string than the original did. For this reason, the overlap calculation described above is repeated using the mirror image of one of the strings, and the maximum of the two is stored as the global maximum for the two strings.

Once the maximum overlap value is determined, a molecular similarity score $Sim_{AB}$ can be defined on the interval from 0 to 1 by normalizing the maximum overlap measured as follows:

$$Sim_{AB} = \frac{S_{max,AB}}{\sqrt{S_{max,AA} S_{max,BB}}}$$

where $S_{max,AB}$ is the maximum measured overlap of string A with string B, and where $S_{max,AA}$ and $S_{max,BB}$ are the maximum measured overlaps of string A and string B with themselves respectively.

Although the speed of comparison using this technique is very fast, it is still desirable to speed the process further, as it can be expected that large libraries of compounds will be screened, and thus even a 5% or 10% savings in computation time can become significant.

One method to speed up the comparison process involves determining those ranges of relative alignment that are likely to contain the global maximum overlap, and performing atom—atom alignments within those ranges first. If one of these ranges in fact contains the global maximum, the remaining alignments need not be evaluated. The two issues to be addressed with such an approach are (1) how to define the ranges so that one knows which ranges to start with, and (2) how to determine when the global maximum has been found without testing all alignments in every range.

Figure 5:
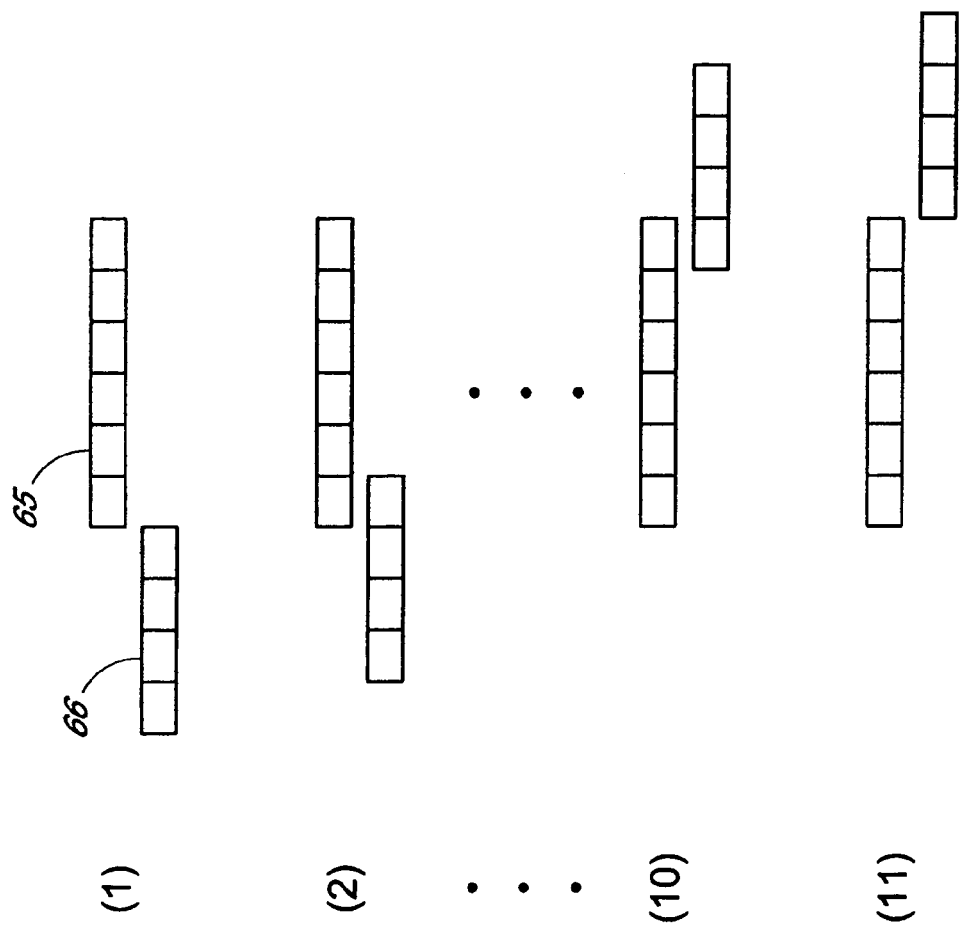
FIG. 5 illustrates two segmented strings aligned at a series of segment aligned orientations.

In one embodiment, this is done by dividing each string into a series of contiguous, non-overlapping segments along each string. It has been found suitable to make the width of each segment equal to w, the same value as the defined width of an atom, although other values could be used. The number of segments a string is divided into is the smallest number that when placed end to end will span the entire length of atomic center coordinates. The series of segments will be slightly longer than the span of atomic center coordinates, and the segments are then centered over the string such that the series of segments extends an equal amount beyond the first and last atomic coordinate. Once the segments are defined, the strings are serially oriented essentially as described above, except the set of relative string orientations is initially selected such that the boundaries of the segments are exactly aligned instead of individual atoms being exactly aligned. This series of segment aligned orientations is illustrated in FIG. 5 for the example situation where upper string A 65 includes six segments, and lower string B 66 includes four segments. There are 11 possible segment boundary aligned orientations as string B slides from left to right past string A. In general, for a first string comprising n segments, and a second string comprising m segments, the total number of possible segment boundary aligned orientations will be n+m+1. At each given segment aligned orientation, an upper bound for the total string overlap is computed for all string orientations within +/−w/2 of that segment aligned orientation, thus producing m+n+1 upper bounds, with each one associated with a narrow range of relative string orientations. As will be discussed in additional detail below, true total string overlaps are first calculated for those narrow ranges of string overlap having the highest upper bounds. This procedure allows for the elimination from consideration many ranges of relative string orientations that have low upper bounds to their overlaps.

Figure 6:
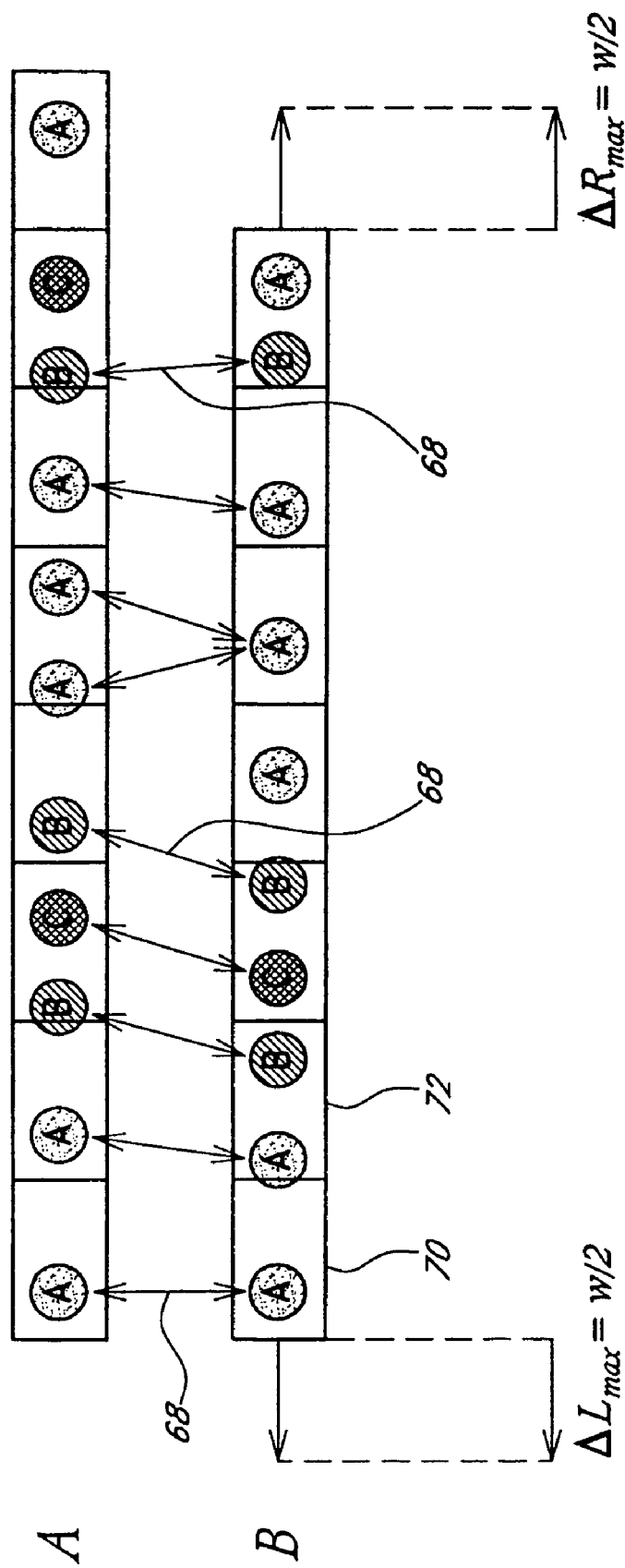
FIG. 6 illustrates two segmented strings aligned at one example segment boundaries.

One method of computing an upper bound for a range of orientations around a selected segment aligned orientation is illustrated by FIGS. 6 and 7. Referring now to FIG. 6, at a given segment boundary alignment, all pairs of matching atom types within one-half segment width (e.g. w/2) of each other are identified. These potential matches are illustrated in FIG. 6 with arrows 68.

Starting at the selected segment boundary aligned orientation, local overlap values separately are computed for each of the individual segments of string B as each individual segment is positioned at the extreme left and right limits of movement +w/2 and −w/2 from the exactly aligned orientation, and at all intermediate positions which exactly align a matching pair of atoms in the shifted individual segment of string B and string A. This is shown in FIGS. 7A through 7C. Referring first to FIG. 7A, overlaps are calculated at all atom based alignments of atoms within the first segment 70 of string B with atoms of the string A as the first segment 70 is moved between w/2 to the left and w/2 to the right of the initial segment aligned relative orientation. The maximum overlap between the atoms in the first segment 70 of string B and the atoms of string A as the segment 70 is moved through this limited extent is stored.

Referring now to FIG. 7B, the same procedure is performed with the second segment 72 of string B. That is, the maximum overlap between the atoms in the second segment 72 of string B and the atoms of string A as the second segment 72 is moved from its initial alignment both left and right by w/2 is stored. As indicated in FIG. 7C, this process is again repeated with the third segment 74 of string B, and successively to all of the individual segments of string B.

Following these computations, all of the stored individual maximum overlaps are added together. As is discussed below with reference to FIGS. 8A–8C, this produces a combined string A–string B overlap value which is guaranteed to be larger than the total string A and string B overlap if this overlap was computed with string A and string B starting at the initial segment alignment and shifted left and right by +w/2 and −w/2 respectively. Thus, an upper bound on the true string overlap is generated within a selected range of orientations having a total width of w and centered around one particular segment aligned orientation.

Figure 8A:
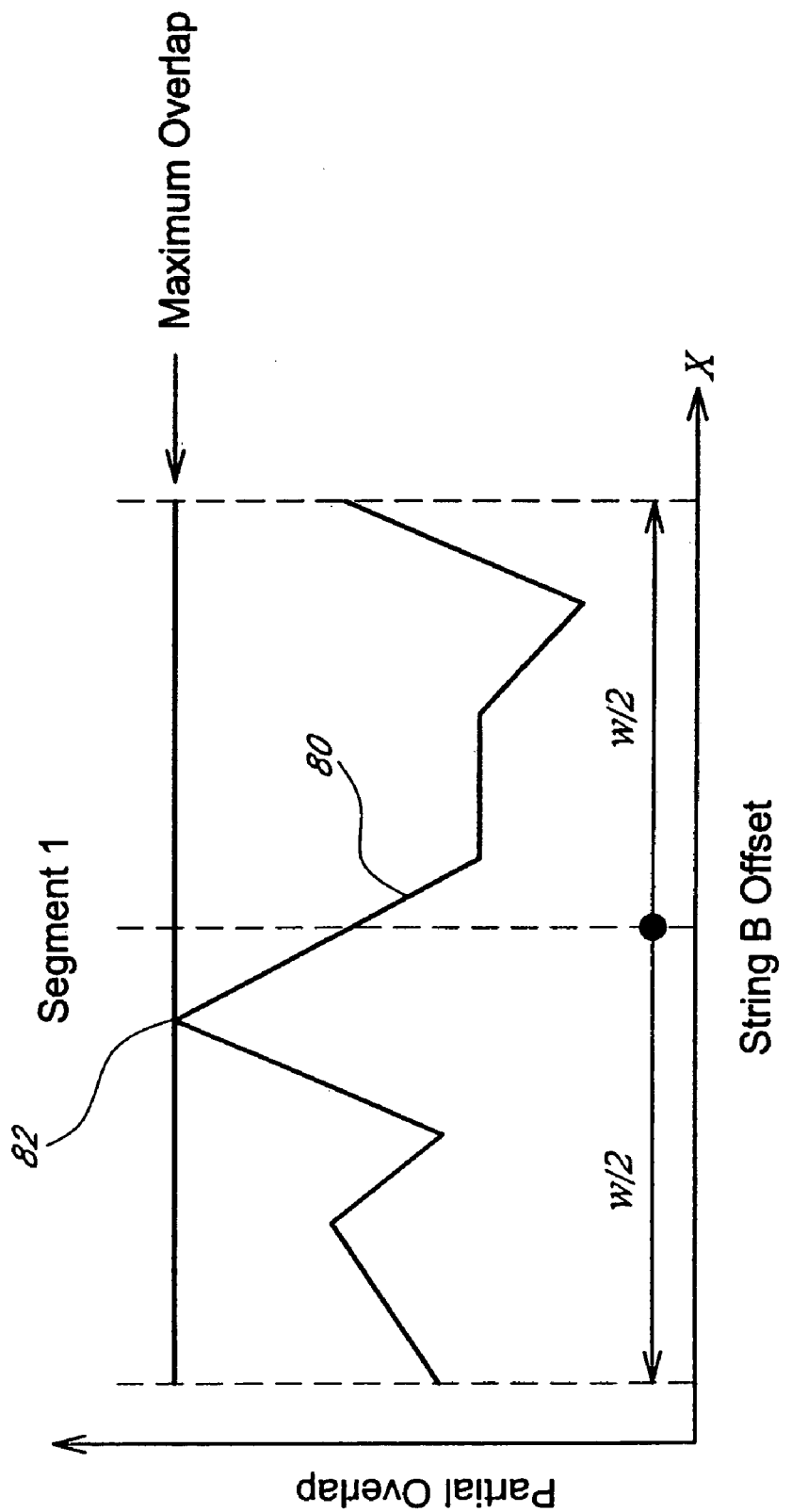
FIGS. 8A–8C illustrate the computation of an upper bound total overlap using individual segment overlaps.
Figure 8B:
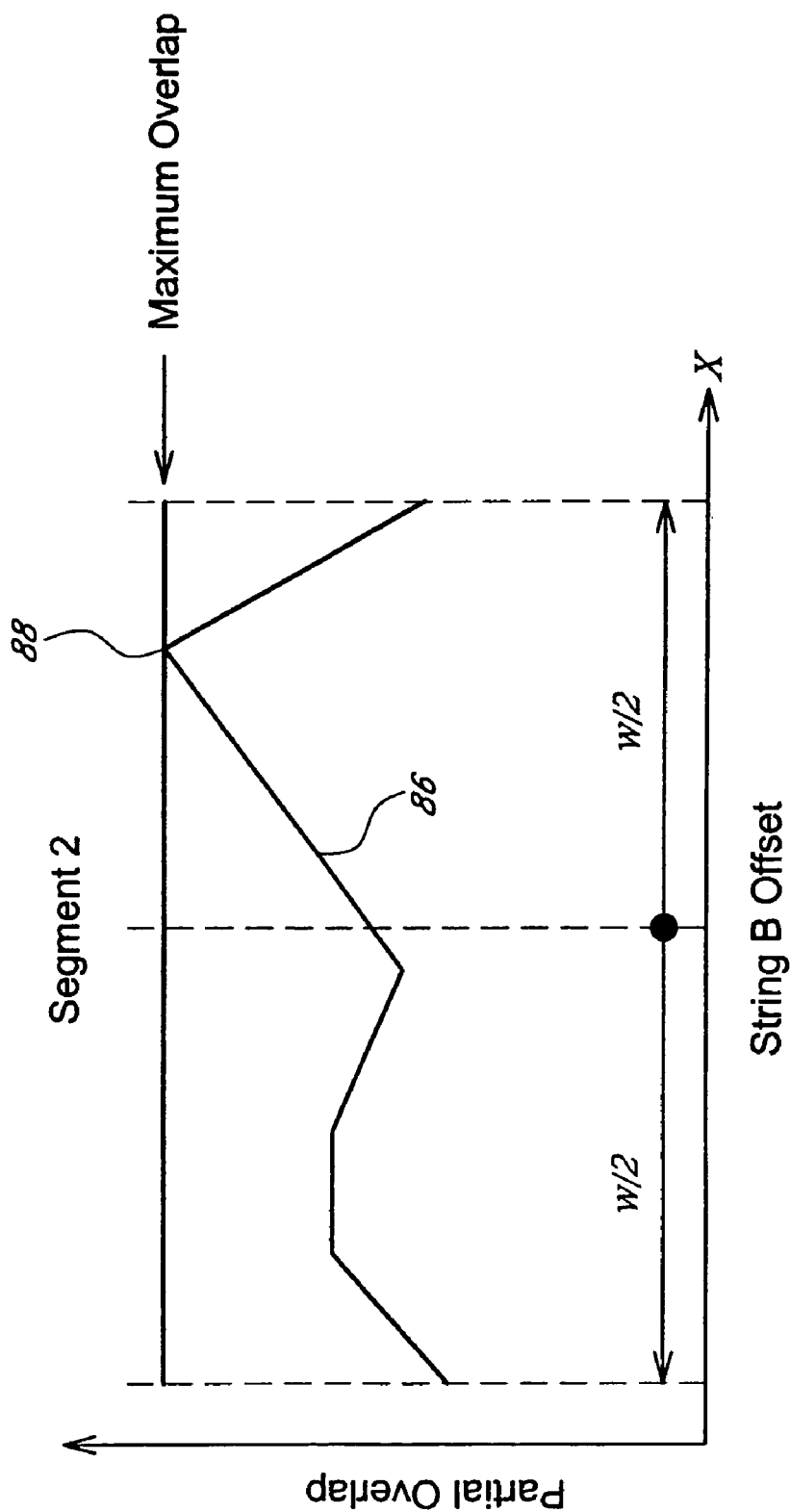
Figure 8C:
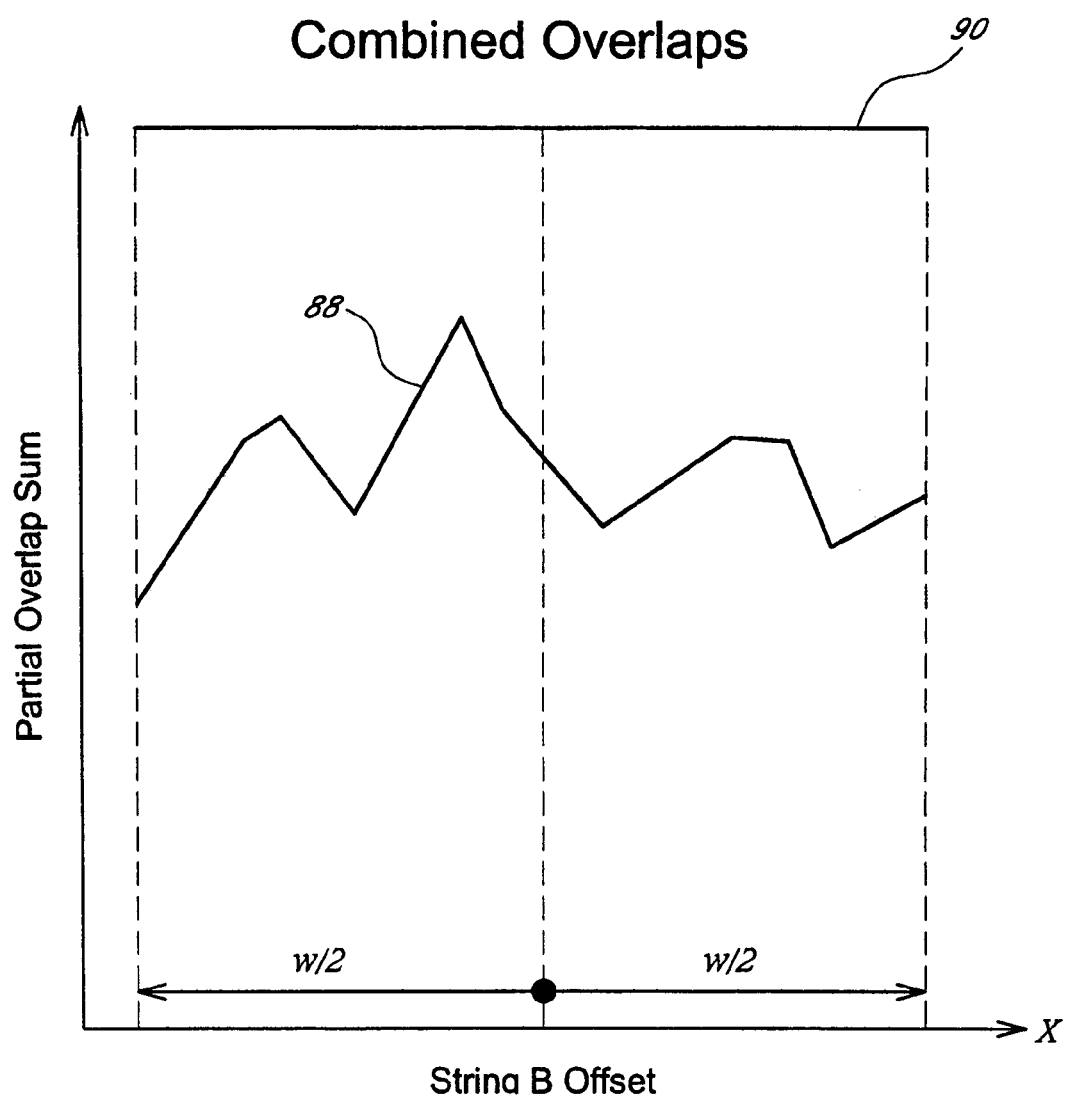

The effect of computing and summing these "partial string" overlaps is shown in FIGS. 8A, 8B, and 8C. Referring to FIG. 8A, curve 80 illustrates the overlap between atoms of string A and a segment of string B as the segment of string B is shifted left and right by w/2 from an initial segment aligned orientation. The peak 82 of this curve 80 defines the maximum partial overlap for this range of string B when moved between these limits. The curve 86 of FIG. 8B illustrates the same true overlap for a second segment of string B. Again, the peak 88 defines the maximum partial overlap for this second segment of string B when moved between these limits.

FIG. 8C illustrates both the sum of the curves 80 and 86 from FIGS. 8A and 8B (designated 88 in FIG. 7C), and the sum of the peak values of these two curves as well (designated 90 in FIG. 8C). The sum of the peak values is higher than the actual sum of the curves. It can thus be appreciated that because the partial overlaps are arrived at by allowing the short segments of string B to move independently of each other during this upper bound calculation process, the true total string overlap is guaranteed to be less than the sum of the peak or maximum partial overlaps. This is true because if molecule B is moved as a single rigid piece, the individual segments will not all simultaneously achieve their best alignments because they are not moving independently. So the maximum partial overlaps can be summed to yield a total overlap area which could never be achieved by movement of the entire rigid molecule B through the same limits.

Using this technique, an upper bound on the possible total string overlap within this range of orientations is calculated. As indicated above, the process described with reference to FIGS. 6 and 7A–7C is repeated at each possible initial string B position having the segments of string B and string A starting out exactly aligned. If, for example, string A is divided into 15 ranges, and string B is divided into 10 ranges, a total of 26 overlap upper bounds will be computed, corresponding to the 26 possible initial segment aligned orientations.

During the actual total string overlap computation, the upper bound overlaps within these ranges of motion are used to eliminate low overlap configurations from detailed consideration. This process is illustrated in FIGS. 9A and 9B. In FIG. 9A, the results of the above described upper bound calculations are graphed, where the string B orientation at each segment aligned position is denoted by its offset in units of w from an orientation in which the central segment of string B is aligned with the central segment of string A. In this example, the highest upper bound 91 results from a consideration of the range (between +w/2 and −w/2) of relative orientations about the segment aligned orientation having the center of string B offset to the left by one segment from the center of string A.

Referring now to FIG. 9B, the total string A/string B overlaps at common atom pair alignments within +w/2 and −w/2 of the segment aligned orientation which has the highest upper bound 91 are computed. In the example of FIG. 9, there are four such atom aligned orientations for which a true full string overlap is computed. If the largest of these overlap values is a computed total string overlap that is larger than the next highest upper bound, overlap evaluations at other atom based alignments need not be performed, because it is not possible for any other string alignment to produce a total overlap greater than its associated upper bound, with the resulting conclusion that no other string alignment can produce an overlap greater than the largest overlap already encountered.

However, if the first range limited search produces a maximum true total string overlap value that is less than the second highest upper bound, overlap calculations at all of the atom based alignments within the range associated with the second highest upper bound are performed. This is illustrated in FIG. 9B as well. In this example, the highest computed true overlap 93 within +/−w/2 of the −w initial position is less than the second highest upper bound 95. Therefore, all atom based alignments between +w/2 and −w/2 of the zero offset initial position are also computed. In the example of FIG. 9B, the highest of these 97 is less than the highest true overlap 93 previously found. Furthermore, the highest true overlap 93 previously found is higher than all of the remaining upper bounds. Therefore, the highest overlap 93 so far calculated is the true highest overlap, and further overlap comparisons need not be performed. In summary, true overlaps are calculated until one is found that is both higher than all of the other computed true overlaps, and also higher than all of the remaining upper bounds. It may then be concluded that further string alignments need not be tested, and the largest overlap found in the previously performed computations is selected as the global maximum overlap value for the two molecules.

Finding the maximum true string overlap is faster with this technique because performing the search in this manner substitutes limited segment overlap calculations for whole string overlap calculation for all atom—atom alignments that are discarded as unnecessary after the true maximum has already been found. Because the upper bound calculation is computationally inexpensive relative to performing full string overlap calculations, this procedure will on average find the true string maximum overlap in about 50% of the time required to perform overlap calculations for the strings as a whole at all common atom—atom alignments. This improvement becomes more pronounced as the molecules being compared increase in numbers of atoms.

It has been found possible to speed the calculation further if the individual segment overlaps are each fit beneath an inverted parabolic curve. In this embodiment, instead of adding the segment overlap peak values to produce an upper bound on the string pair overlap, the series of parabolic curves are added, and the value of the apex of the summed parabolas is taken as the upper bound for that range of string B motion. This process is illustrated in FIGS. 10A–10C.

Figure 10A:
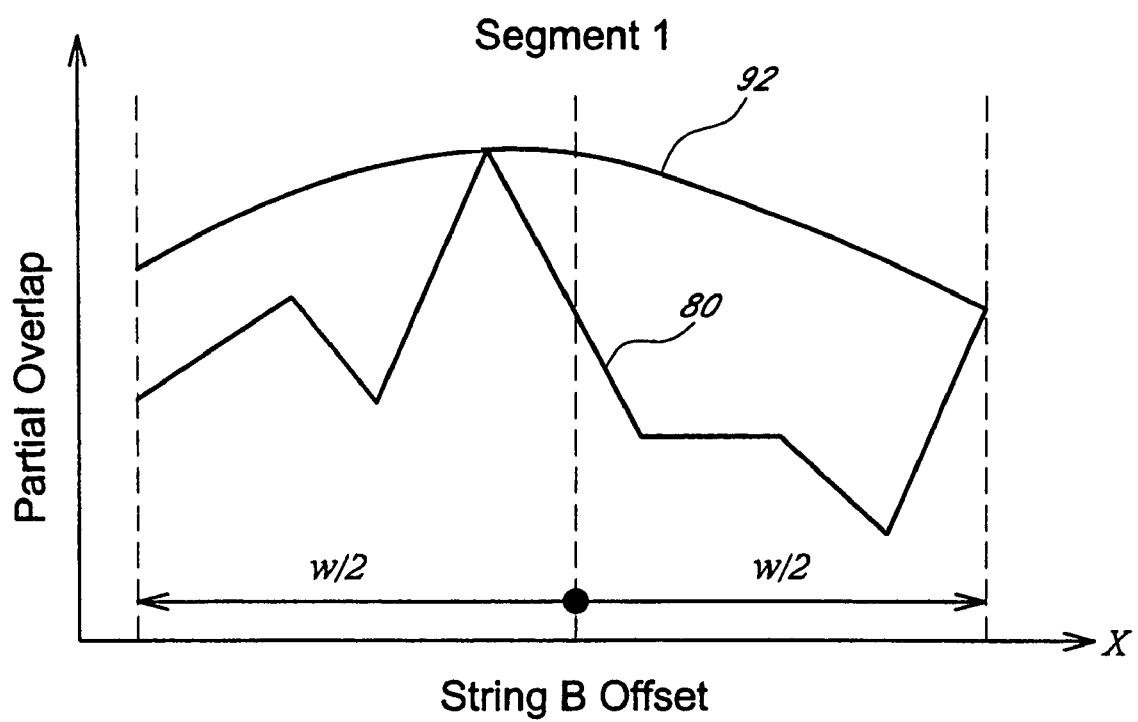
FIGS. 10A–10C illustrate an alternative computation of an upper bound total overlap using individual segment overlaps.
Figure 10B:
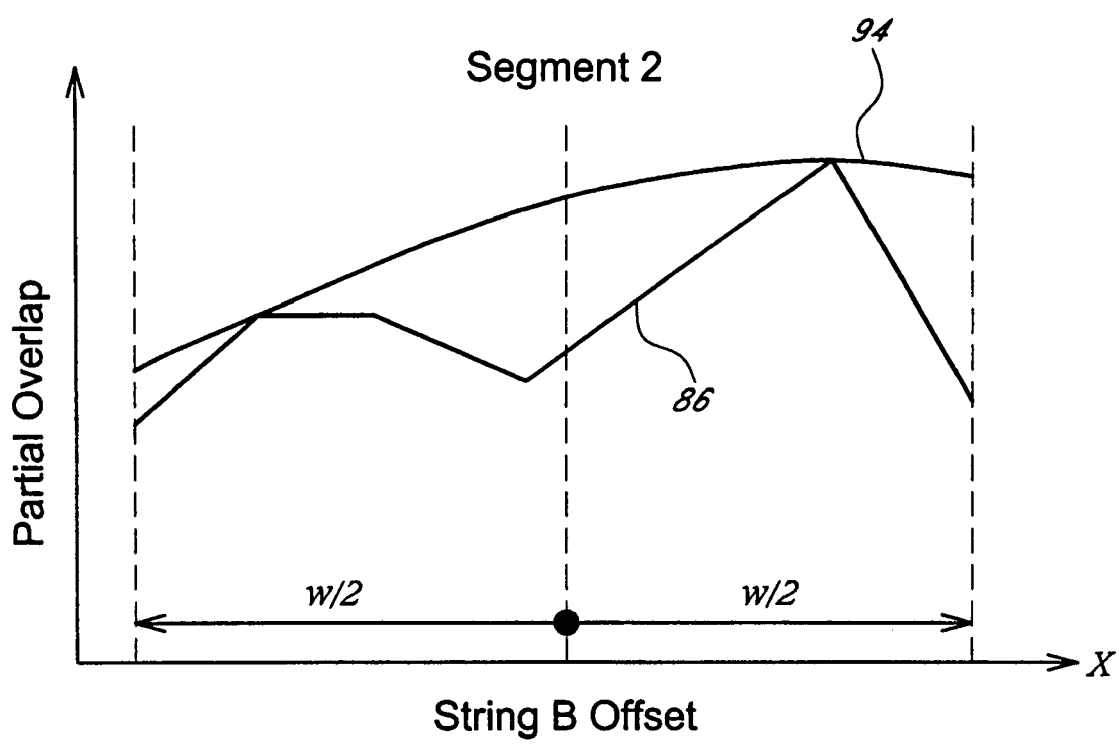
Figure 10C:
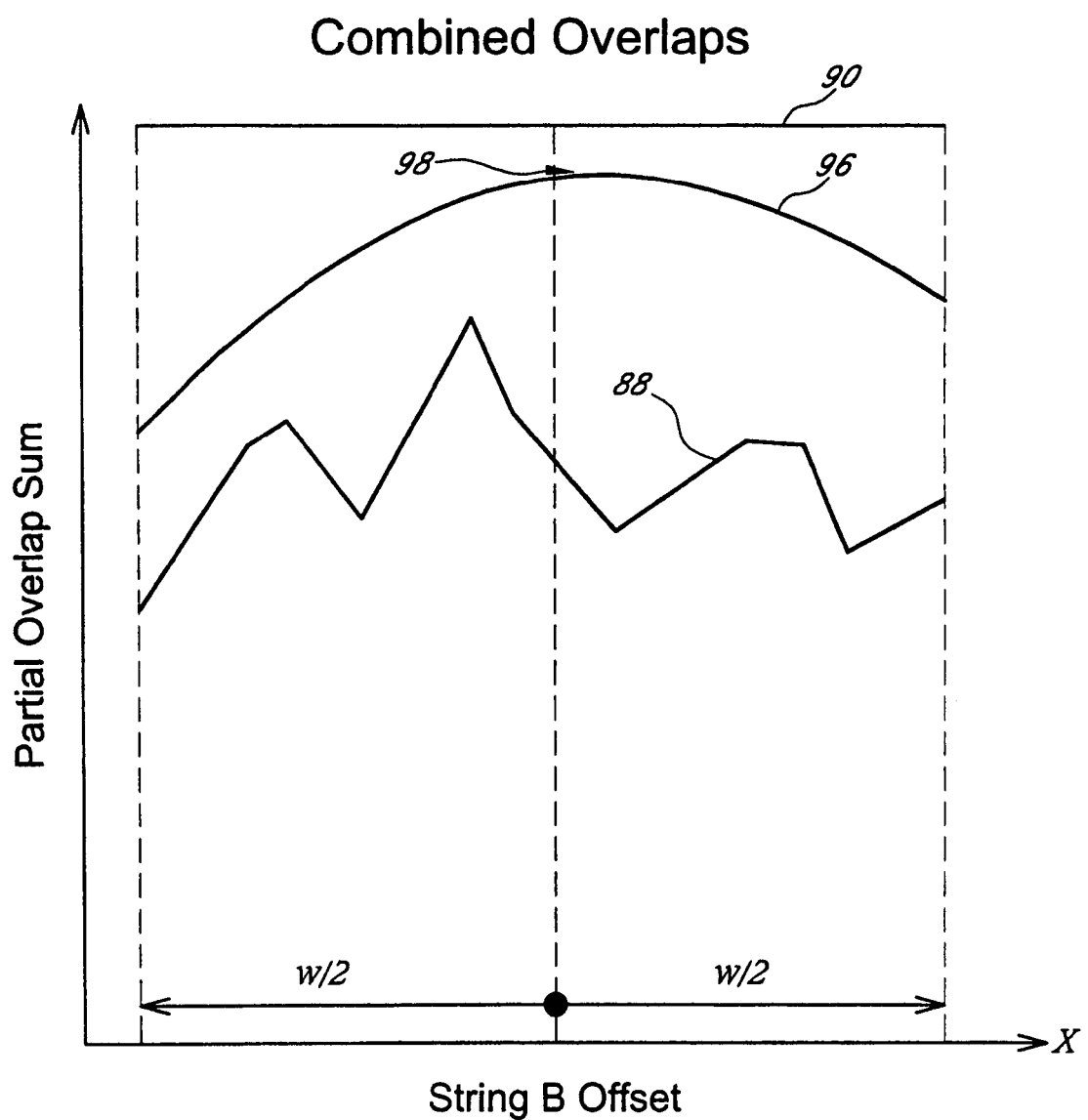

FIGS. 10A and 10B show the same segment overlap curves 80, 86 as are shown in FIGS. 8A and 8B respectively. However, instead of simply storing the peak value, inverted parabolas 92, 94 are defined having their apex coinciding with the highest peak and passing through the next highest peak so that the curve always remains above the true segment overlap value. These parabolas may be summed by summing the coefficients of their $x^2$, x, and constant terms respectively, as shown in FIG. 10C by parabola 96. Because the apexes of the different parabolas are not coincident in the x dimension, the summed parabola 96 will have an apex 98 which is lower than the arithmetic sum of the peaks (designated at 90) shown in FIG. 8C. The overlap value at the apex of the sum parabola (i.e. the maximum height) is taken as the upper bound for that range of motion of string B.

This procedure requires the computation of the coefficients of many quadratic equations. However, by lowering the estimated upper bounds, termination of the search procedure tends to occur earlier. The net result is an average decrease in search time of about 10–15% from the simple summing of peak values described with reference to FIGS. 8A–8C.

As mentioned above, the comparison process is performed twice, the second time using a mirror image of one of the linear representations. It will be appreciated that when string A and string B are relatively similar in one linear representation of molecule B, they will usually be quite dissimilar in the alternative mirror image linear representation of molecule B. Because of this, it is advantageous to perform the overlap calculation using that linear representation containing the true largest overlap first. When the upper bound calculation process is then performed with the mirror image representation, it is typical for most if not all of the computed upper bound values for the mirror image to be lower than the largest overlap value found during the first comparison process. All overlap calculations in these ranges for the mirror image representation can be avoided when this occurs, and very early termination of the overlap search with the mirror image molecule B typically occurs.

Although it is not known with certainty before hand which of the two mirror image representations of string B actually produces the true maximum overlap, a very simple comparison of string A with the two different representations of string B can be made that allows a reasonably accurate prediction to be made as to which of the two mirror image representations is more likely to contain the global maximum overlap.

To perform this comparison, string A and string B are oriented with their centers aligned. Then, the position of string B is shifted to align, as closely as possible, common atom pairs between the two strings. The amount of this shift $\Delta x_B$ is calculated as follows:

$$\Delta x_B = \frac{1}{N_{match}} \sum_{\substack{Common \\ atom \\ pairs}} (x_A - x_B)$$

wherein $N_{match}$ is the total number of matching atom pairs between string A and string B. This shift produces the best possible average alignment of common atom pairs.

After aligning the strings in this way, the squares of the linear offsets between all atom pairs of the same class in string A and string B is computed to produce a sum-squared-deviation (SSD) as follows:

$$SSD = \sum_{\substack{Common \\ atom \\ pairs}} (x_A - x_B)^2$$

This provides a rough measure of how far apart in the representations common atoms are located. This procedure is then performed again with the mirror image of string B. Whichever representation produces a lower sum with respect to string A is tested first for the total maximum global overlap.

As described above, the molecule B linear representation having the lowest SSD with string A is compared with string A for maximum overlap first. When string A and string B are more than 80% similar, the above procedure picks the correct starting orientation of string B about 90% of the time.

Figure 11:
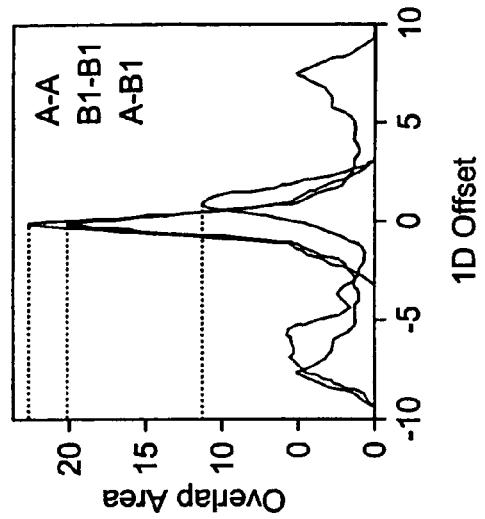
FIG. 11 illustrates a comparison of two compounds using techniques in accordance with the invention.
Figure 11:
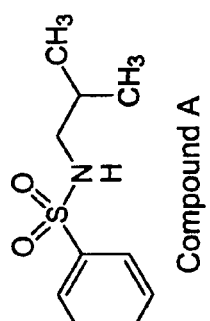
Figure 11:
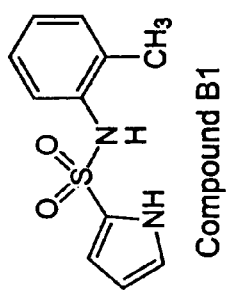
Figure 11:
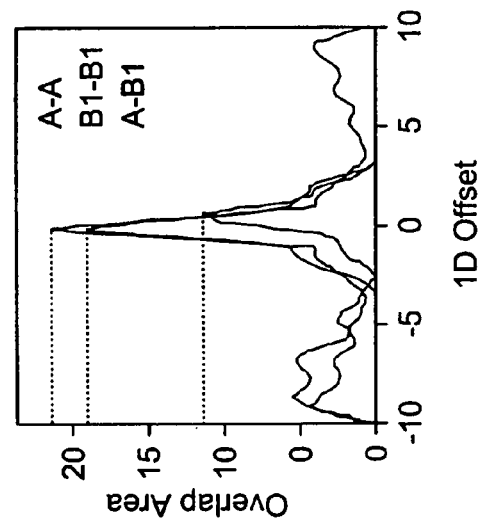
Figure 12:
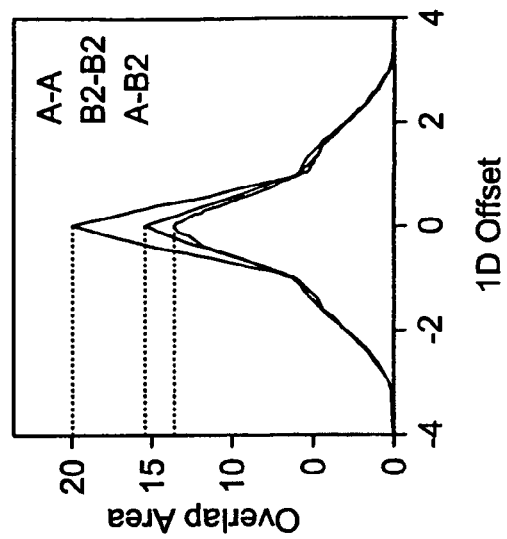
FIG. 12 illustrates a comparison of two compounds using techniques in accordance with the invention.
Figure 12:
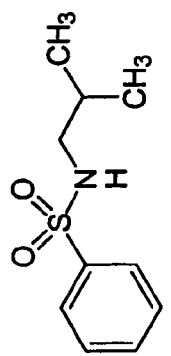
Figure 12:
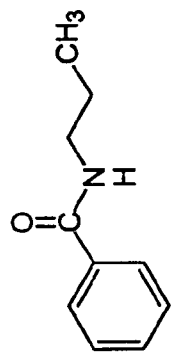
Figure 12:
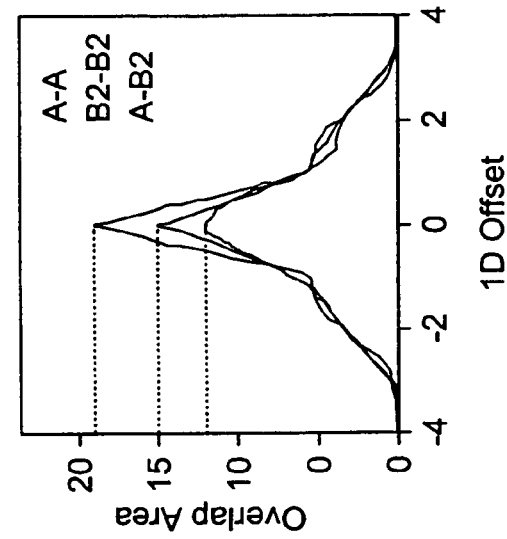

FIGS. 11 and 12 illustrate the results of a comparison between a first compound, denoted compound A with two other compounds, denoted B1 and B2. Similarity calculations were performed using both 3D atomic coordinates to derive 1D representations, and also using 2D topological information to derive 1D representations. FIG. 11 shows the result of the comparison between compound A and compound B1 when 3D and 2D information was used as a starting point. FIG. 12 shows the result of the comparison between compound A and compound B2 when 3D and 2D information was used as a starting point. Although graphs of overlap as a function of offset are shown in FIGS. 11 and 12 for illustrative purposes, it will be appreciated that in accordance with the above described techniques, most of the computations needed to generate such graphs are not required to be performed in order to produce the desired similarity measure. Using the equation:

$$Sim_{AB} = \frac{S_{max,AB}}{\sqrt{S_{max,AA} S_{max,BB}}}$$

the similarity value $Sim_{AB1}$ for compounds A and B1 is 0.564, when 3D coordinates are used to derive the 1D representations, and is 0.529 when 2D topology is used to derive the 1D representations. In addition, the similarity value $Sim_{AB2}$ for compounds A and B2 is 0.709, when 3D coordinates are used to derive the 1D representations, and is 0.775 when 2D topology is used to derive the 1D representations.

The A-B2 similarity is greater than the A-B1 similarity primarily because the right side of B2 contains an alkyl chain that matches up well with the alkyl chain of compound A, whereas compound B1 has an aromatic ring in that location. There is some additional loss of similarity for B1 because the aromatic ring on the left side of compound A is replaced by a five member nitrogen containing ring. For B2, the loss of the methyl group at the end of the alkyl chain and the substitution of an amide group for the sulfonamide of compound A does not diminish the similarity as much as the above mentioned mismatches between compound A and compound B1. Compound B2 would thus be predicted to be more likely to display similar chemical behavior to that exhibited by compound A.

When libraries of compounds (referred to below as the set of B molecules) are to be compared to a selected molecule (referred to below as the A molecule), additional techniques can be devised to speed the total library comparison process. In one such method, true overlap calculations are not performed at all for any B molecule from the library which is guaranteed to have an overlap with the A molecule below some pre-defined threshold value. In other words, low overlap molecules are essentially ignored. This is acceptable because interest is typically limited to high overlap molecules, and performing similarity calculations on a large number of low overlap compounds is not particularly useful. In one specific version of this embodiment, a technique having similarities to the calculations described above with respect to FIGS. 5–10 is performed to determine upper limits of A-B overlaps quickly. If the upper limit for a given molecule B is below the threshold, no true overlap computations are performed for that molecule of the library.

Figure 13:
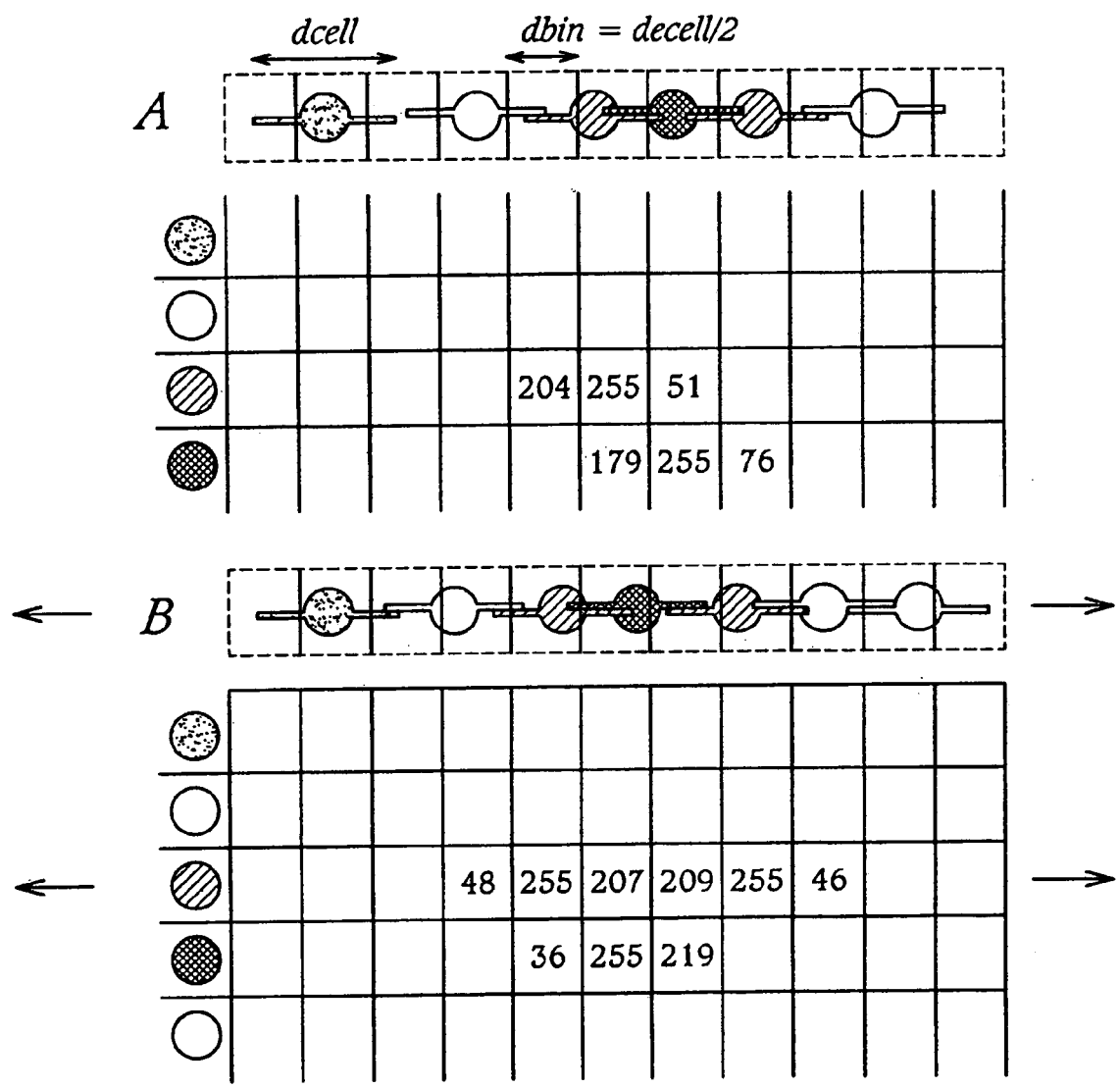
FIG. 13 is an illustration of segment based overlap estimation calculation.

In one embodiment, illustrated in FIG. 13, the real A-B overlap may be estimated by another segment based computation. In this embodiment, each string is segmented into a series of contiguous bins. The width of each bin may vary, but ½ of the atomic width has been found suitable for this process (in contrast with the segments of width equal to atomic width as described above). If the bin width is ½ of the defined atom width, each atom is spread over three bins, unless its center coincides exactly with a bin boundary, in which case it will occupy exactly two bins. For each atom, an integer "occupation number" from 0 to 255 is assigned to each bin the atom resides in. This occupation number is a measure of how much of a bin an atom occupies. If the atom spans the bin completely, the occupation number is 255. If the atom occupies ⅛ of a bin, the occupation number for that bin is 32.

At each bin aligned A-B orientation, the occupation numbers for the same atom type in each aligned bin are multiplied, and these values from the series of bins are added. If this process is performed at all possible bin aligned orientations, the maximum value computed can be scaled and used to give a value for maximum possible total overlap if the value is further inflated to account for errors introduced by the discrete nature of the bins. Thus, an upper limit to the total A-B overlap may be taken to be the largest bin aligned estimate produced by the multiplication and sum described above multiplied by the factor $[1+((bin\ width)/2\ (atom\ width))]$. If the bin width is half the atomic width, this results in a 25% increase in the estimate to produce the upper bound. If this upper bound is below a pre-defined threshold, the molecule may be eliminated from consideration for future exact overlap calculations.

Figure 14:
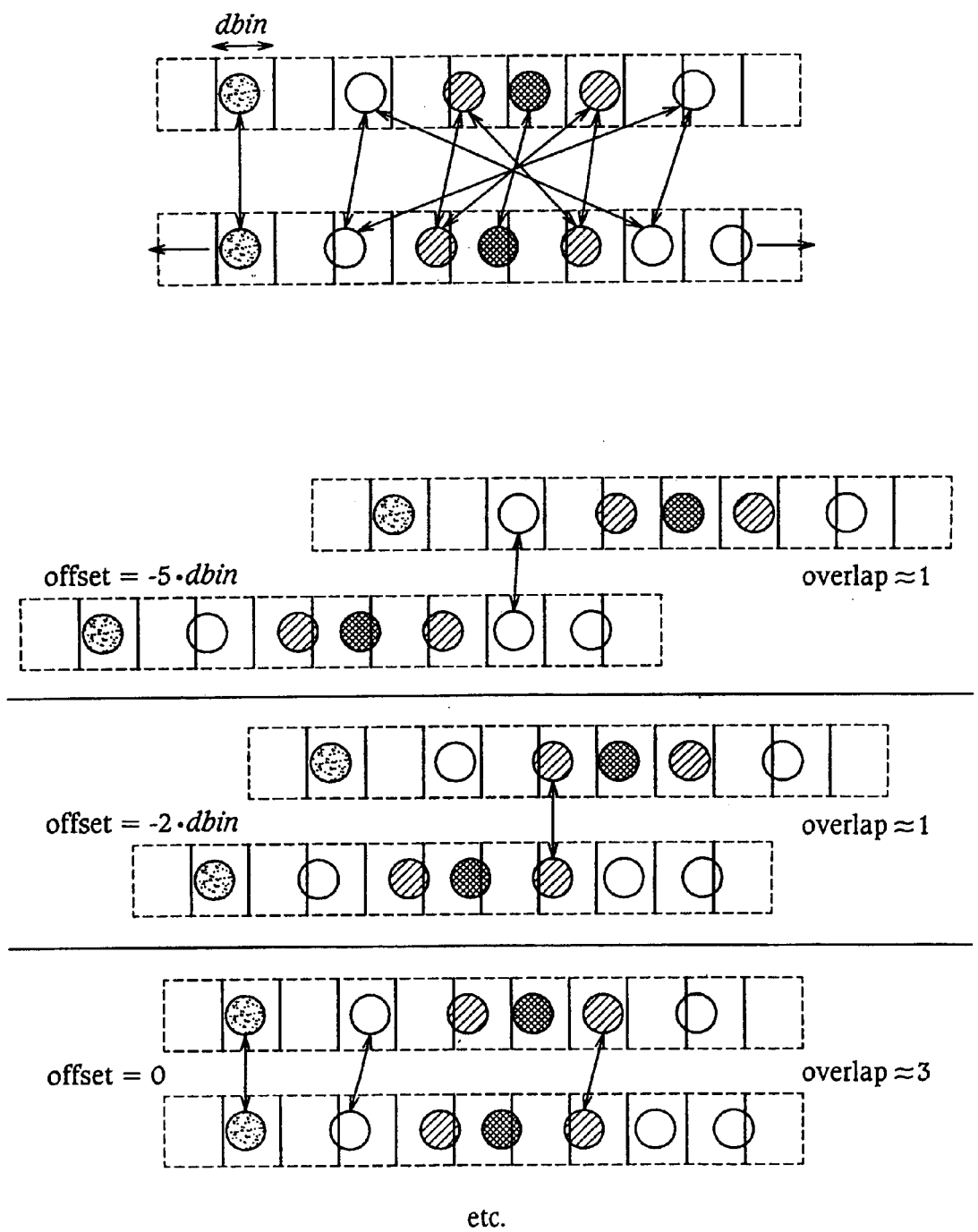
FIG. 14 is an illustration of integer upper bound calculations to reduce the number of segment based overlap estimates required.
Figure 15:
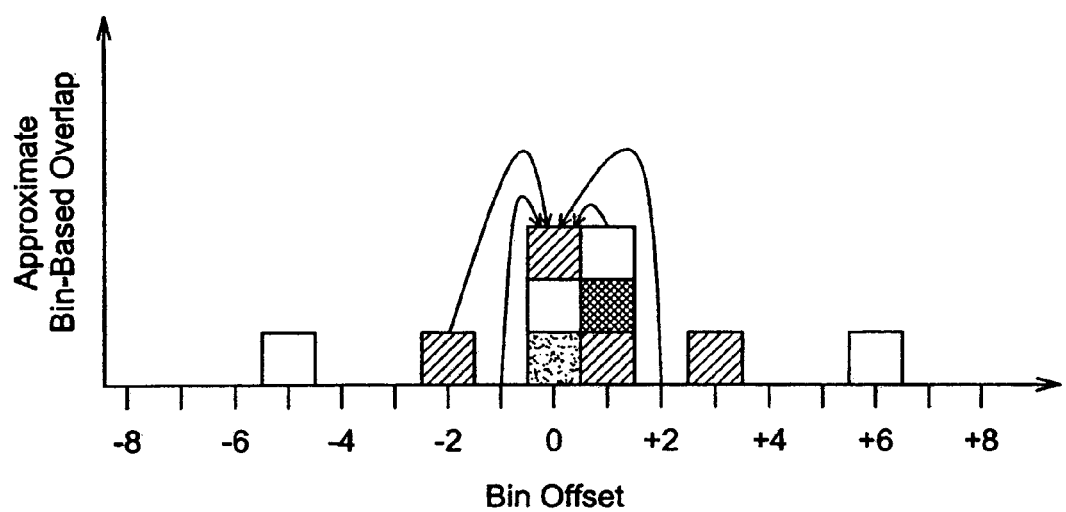
FIG. 15 is an illustration of integer upper bound calculations for reducing the number of segment based overlap estimates required.
Figure 15:
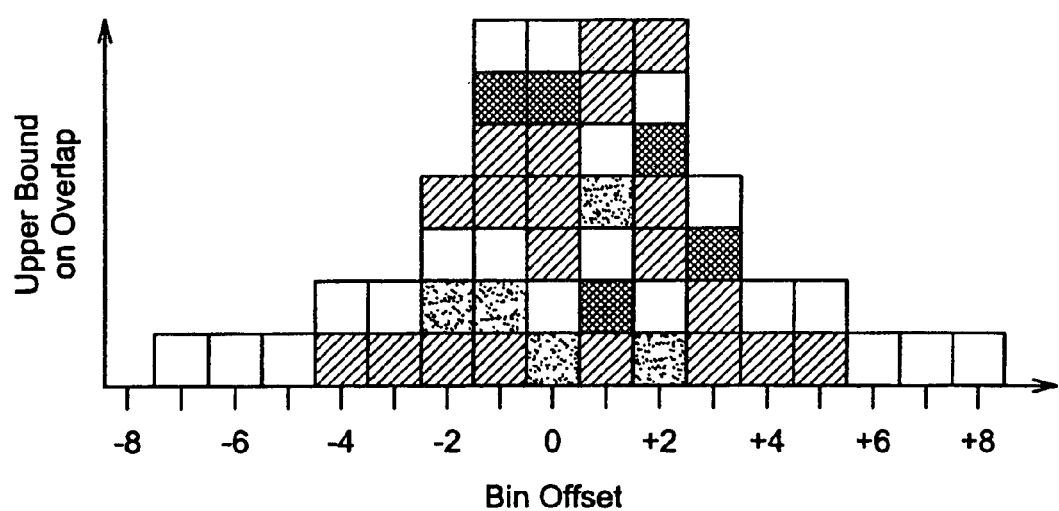

Although this procedure is fast, one problem with it is the fact that there are usually a large number of bin aligned orientations to consider. This number can be reduced in a manner analogous to that described above by computing upper bounds for each bin aligned position, and then eliminating from consideration those bin aligned orientations having upper bounds lower than a previously computed estimate. This is illustrated in FIGS. 14–15.

To eliminate some bin aligned orientations from consideration, those bin aligned orientations having one or more common atom pairs with centers in aligned bins are found. For each one of these pairs, an overlap value of one is added to a total overlap value for the two strings at this orientation, thus producing an integer overlap value corresponding to a count of the common atom pairs having their centers in aligned bins. Because two atoms may be overlapping, but have their centers in non-aligned bins, a strict upper bound for a given bin aligned orientation may be taken to be the sum of the integer values for all the bin aligned positions within plus or minus two bin offsets from the one computed. For the molecules of FIG. 14, for example, the upper bound is taken to be seven rather than three for the zero offset bin aligned orientation. The method of combining the totals from nearby offsets to determine the strict upper bounds is shown in FIG. 15. The cross-hatching of the boxes indicate the different atom types that contribute each unit of approximate overlap. Once these upper bounds are computed, actual estimates using the occupation numbers as described above are performed for the bin aligned offsets having the highest upper bounds first. As above, once a real estimate has been produced which is higher than all remaining upper bounds, the computation may terminate, and the highest estimate is used to determine the upper limit of total overlap for the two molecules.

In test of this procedure where 99% of the molecules of the library are below the overlap threshold, about 95% of these low overlap molecules are eliminated from this process, producing about a five-fold increase in the speed of library analysis.

It has also been found that ligands for a given target tend to have 1-D similarities of greater than about 0.5. This may be used to rank libraries or sub-libraries such that screening and design can be guides by ranking. One suitable library ranking comprises the formula: library rank=$s/(n*m)$, where s is the number of compounds in the library having 1D similarities of greater than 0.5, n is the number of compounds in the library, and m is the number of active lead compounds.

The above molecular representations thus provide a means for efficient molecular comparisons, avoiding several computational difficulties present in the prior art. One-dimensional representation surprisingly affords, in many cases, a more valid means of comparing structures than other well established methods based on either two or three dimensional representations. While providing a distinct advantage in speed over three-dimensional approaches. Thus, the drug discovery process may be performed with greater combined speed and effectiveness with the above described invention than has heretofore been possible.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method of predicting functional similarity between two molecules comprising:

deriving a first one-dimensional representation of a first molecule with a known chemical behavior from distances between selected atoms of said first molecule, said one dimensional representation comprising a string of atoms, each atom of said string having a selected type, a selected width, and a selected position along said string;

deriving a second one-dimensional representation of a second molecule with an unknown chemical behavior from distances between selected atoms of said second molecule, said one dimensional representation comprising a string of atoms, each atom of said string having a selected type, a selected width, and a selected position along said string; and comparing said one dimensional representations, wherein the comparing comprises:

aligning the one dimensional representations such that the position of an atom of a first selected type in the first one dimensional representation coincides with the position of an atom of the first selected type in the second one-dimensional representation; and evaluating the amount of overlap between atoms of each selected type in the first one-dimensional representation and atoms of the same type in the second one-dimensional representation; and identifying the second molecule as likely to have similar chemical behavior as the first molecule based on said comparing.

2. The method of claim 1, wherein said positions in the first one-dimensional representation are selected to reduce the deviation between relative positions of the atoms in the string of atoms and three dimensional distances between the atoms in said first molecule.

3. The method of claim 1, wherein the atoms of the first selected type in the first and second one-dimensional representations have the same element type.

4. The method of claim 3, wherein the atoms of the first selected type in the first and second one-dimensional representations have the same hybridization state.

5. The method of claim 1, wherein at least some of said distances are derived from molecular topology.

6. The method of claim 5, wherein at least some of said distances are derived from bond counts.

7. The method of claim 1, wherein at least some of said distances are derived from three dimensional atomic coordinates.

8. The method of claim 1, wherein at least some relative positions of the atoms in the one-dimensional representations are not equal to corresponding three dimensional distances between the same atoms in the molecules.

9. A computer-implemented method of selecting for further testing and analysis a subset of molecules from a library of molecular structures, said method comprising:

storing one-dimensional representations of said molecular structures in a database, said one-dimensional representations being derived from three dimensional distances or topological distances between atoms of said molecular structures, wherein said one dimensional representations comprise strings of atoms, each atom of each string having a selected type, a selected width, and a selected position along the string;

deriving a one-dimensional representation of a molecule having known biochemical activity from three dimensional distances or topological distances between atoms of said molecule; wherein at least some of the atoms of said molecule are assigned positions in a one-dimensional representations of the molecule, wherein the one dimensional representation of the molecule comprises a string of atoms, each atom of the string having a selected type, a selected width, and a selected position along the string;

comparing said one-dimensional representation of said molecule having known biochemical activity with said one-dimensional representations of said molecular structures in said database, wherein the comparing comprises:

aligning the one dimensional representation of said molecule with the one-dimensional representations of said molecular structures such that the position of an atom of a first selected type in the one dimensional representation of said molecule coincides with the position of an atom of the first selected type in the one-dimensional representations of said molecular structures; and evaluating the amount of overlap between atoms of each selected type in the one-dimensional representation of said molecule and atoms of the same type in the one-dimensional representation of said molecular structures; and identifying a molecular structure of said molecular structures as likely to have similar chemical behavior as said molecule based on said comparing.

10. A computer readable storage medium having stored thereon structural representations of molecules for retrieval by a computer implemented molecular screening program, wherein at least one of said structural representations comprises a list of selected atoms in said molecule, wherein each of said selected atoms is associated with an atom type, a selected width, and a selected position along a one-dimensional string of atoms.

11. The storage medium of claim 10, wherein said selected position is derived from distances between said selected atoms in said molecule.

12. The storage medium of claim 11, wherein said distances comprise three dimensional distances.

13. The storage medium of claim 11, wherein said distances comprise topological distances.

* * * * *